United States Patent
Ashby et al.

(10) Patent No.: US 6,518,035 B1
(45) Date of Patent: Feb. 11, 2003

(54) TARGETED METHODS OF DRUG SCREENING USING CO-CULTURE METHODS

(75) Inventors: Matthew Ashby, Mill Valley, CA (US); Daniel D. Shoemaker, Bothell, WA (US)

(73) Assignee: Rosetta Inpharmatics, Inc., Kirkland, WA (US)

(*) Notice: Subject to any disclaimer, the term of this patent is extended or adjusted under 35 U.S.C. 154(b) by 0 days.

(21) Appl. No.: 09/454,889

(22) Filed: Dec. 3, 1999

Related U.S. Application Data

(63) Continuation-in-part of application No. 09/213,120, filed on Dec. 15, 1998, now abandoned, which is a continuation of application No. PCT/US98/11415, filed on Jun. 2, 1998.

(51) Int. Cl.$^7$ .............................. C12Q 1/00; C12Q 1/68; C12Q 1/34; G01N 33/53

(52) U.S. Cl. ................... 435/18; 435/4; 435/6; 435/7.71

(58) Field of Search .............................. 435/6, 7.71, 4, 435/18

(56) References Cited

U.S. PATENT DOCUMENTS

| | | |
|---|---|---|
| 4,980,281 A | 12/1990 | Housey |
| 6,046,002 A | 4/2000 | Davis et al. |

FOREIGN PATENT DOCUMENTS

| | | |
|---|---|---|
| EP | 0679716 | 11/1995 |
| EP | 0887415 | 12/1998 |
| EP | 0887416 | 12/1998 |
| WO | Wo 95/06132 | 3/1995 |
| WO | WO 98/05786 | 2/1998 |
| WO | WO 95/54333 | 12/1998 |

OTHER PUBLICATIONS

Gonzalez et al. Intracellular detection assays for high–throughput screening. Current Opinion in Biotechnology (1998) 9:624–631, Dec. 1998.*

Cubitt et al. Understanding, improving, and using green fluorescent proteins. TIBS (1995) 20:448–455, Nov. 1995.*

Hausner et al. The "Comparative Growth Assay": Examining the Interplay of Anti-cancer Agents with Cells Carrying Single Gene Alterations. Neoplasia (1999) 1(4):356–367, Oct. 1999.*

Fink et al. The effect of different chemotherapeutic agents on the enrichment of DNA mismatch repair–deficient tumour cells. British Journal of Cancer (1998) 77(5):703–708, Mar. 1998.*

Parent et al. Mutations of Two Adjacent Amino Acids Generate Inactive and Constitutively Active Forms of the Human Platelet–activating Factor Receptor. Journal of Biological Chemistry (1996) 271(14):7949–7955, Apr. 1996.*

Sittampalam et al., 1997, "High–throughput screening: advances in assay technologies," Curr. Opin. Chem. Biol. 1(3):384–91.

Freshney, Culture of Animal Cells, Ch. 19, pp. 287–307 ($3^{rd}$ ed. 1996).

Freshney, Culture of Animal Cells, Ch. 12, pp. 179–195 ($3^{rd}$ ed. 1996).

Shoemaker et al., 1996, "Quantitative phenotypic analysis of yeast deletion mutants using a highly parallel molecular bar–coding strategy," Nature Genetics 14:450–56.

Bohmer et al., 2001, "Fetal and Maternal Progenitor Cells in Co–Culture Respond Equally to Erythropoietin," Prenat. Diagnosis 21:818–823.

Simon et al., 2001, "Luminescent Method for the Detection of Antibacterial Activities," Appl. Microbiol. Biotechnol. 57:757–763.

Torrance et al., 2001, "Use of Isogenic Human Cancer Cells for High–througput Screening and Drug Discovery," Nature Biotechnology 19:940–45.

Genbank Accession No. Z95586 (Mycobacterium tuberculosis H37Rv).

EMBL Database Emest16, entry MMAA68614, Accession No. AA168614, Dec. 22, 1996.

EMBL Database Emest13, entry HSW4115, Accession No. W96411, Jul. 18, 1996.

EMBL Database Emest15, entry MM3448, Accession No. W14344, Apr. 30, 1996.

EMBL Database Emest12, entry HSAA19855, Accession No. AA210930, Feb. 2, 1997.

EMBL Database Emest8, entry HS181310, Accession No. N76181, Apr. 5, 1996.

EMBL Database Emest8, entry HS1228356, Accession No. AA428315, May 25, 1997.

EMBL Database Emest16, entry MMAA21859, Accession No. AA012859, Nov. 29, 1996.

(List continued on next page.)

*Primary Examiner*—Ponnathapura Achutamurthy
*Assistant Examiner*—Manjunath N. Rao
(74) *Attorney, Agent, or Firm*—Pennie & Edmonds LLP

(57) ABSTRACT

The present invention provides methods of screening for a molecule that inhibits the expression or activity of a protein encoded by a target gene which affects the fitness of a cell. The methods are based on a co-culture assay, and entail culturing together two cell populations, each of which is a population of identical cells, of the same species that differs substantially only in the expression or activity of the gene to be targeted or its encoded protein and the presence or absence of a reporter gene. The screen can be applied to cultured cells, unicellular and multicellular organisms. Manipulating the expression or activity of the target gene sensitizes the host to a molecule which inhibits the target gene or its encoded protein such that the cell or organism comprising the manipulated target gene grows at a different rate from the cell or organism comprising the unmanipulated gene in response to exposure to the molecule. The methods of the invention can be used for identifying drugs, proteins or any other molecules that inhibit the function of proteins encoded by target genes.

107 Claims, 3 Drawing Sheets

OTHER PUBLICATIONS

Figure 1A:
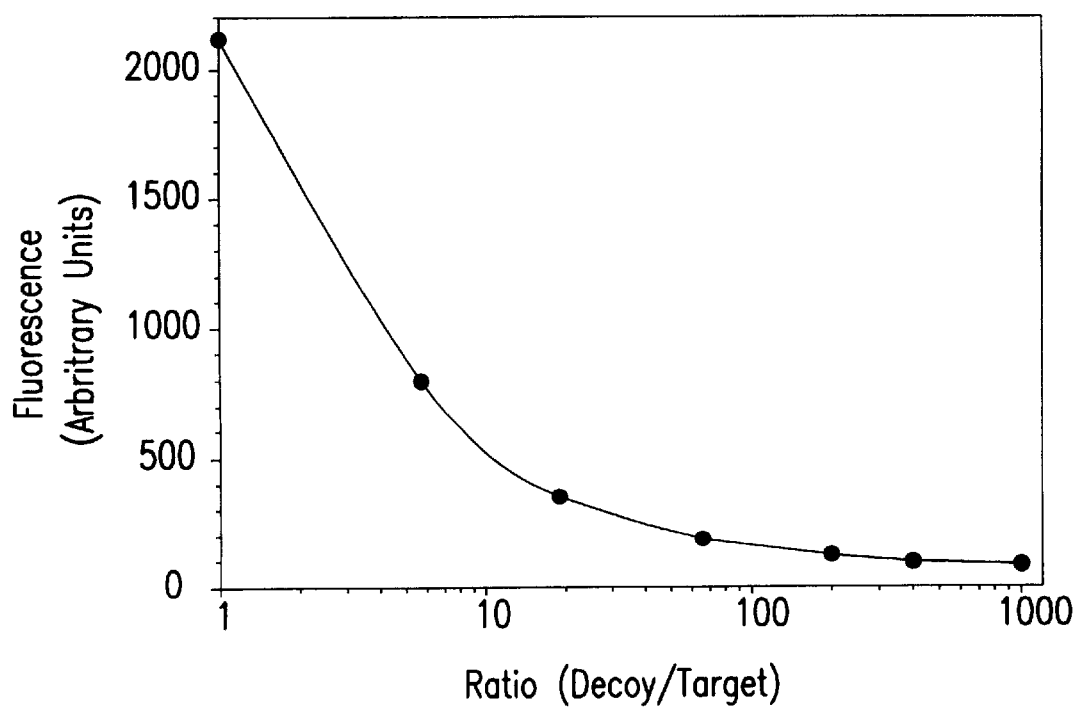

EMBL Database Emest18, entry HSZZ64182, Accession No. AA359058, Apr. 18, 1997.

Akopyan et al., 1994, "Proteolytic processing of farnesylated peptides: assay and partial purification from pig brain membranes of an endopeptidase which has the characteristics of E.C.3.4.24.15", Biochem. Biophys. Res. Comm. 198:787–794.

Assaraf et al., 1989, "Sequential amplification of dihydrofolate reductase and multidrug resistance genes in Chinese hamster ovary cells selected for stepwise resistance to the lipid–soluble antifolate trimetrexate", J. Biol. Chem. 264:18326–18334.

Banerjee et al., 1994, "inhA, a gene encoding a target for isoniazid and ethionamide in Mycobacterium tuberculosis" Science 263:227–230.

U.S. patent application Ser. No. 09/213,120, Ashby et al., filed Dec. 15, 1998.

Blattner et al., 1997, "The complete genome sequences of Escherichia coli K–12", Science 277:1453–1474.

Boyartchuk et al., 1997, "Modulation of Ras and a–factor function by carboxyl–terminal proteolysis", Science 275:1796–1800.

Chen et al., 1996, "Solubilization, partial purification and affinity labeling of the membrane–bound isoprenylated protein endoprotease", Biochem. 35:3227–3237.

Chopra et al., 1997, "The search for antimicrobial agents effective against bacteria resistant to multiple antibiotics", Antimicrob. Agents Chemother. 41:497–503.

Clewell et al., 1975, "Plasmid–determined tetracycline resistance in Streptococcus faecalis: evidence for gene amplification during growth in presence of tetracycline", Proc. Natl. Acad. Sci. USA 72:1720–1724.

Cohen, 1992, "Epidemiology of drug resistance: implications for a post–antimicrobial era", Science 257:1050–1055.

Driscoll et al., 1989, "Genetic and molecular analysis of a Caenorhabditis elegans beta–tubulin that conveys benzimidazole sensitivity", J. Cell Biol. 109:2993–3003.

Espinet et al., 1995, "An efficient method to isolate yeast gene causing overexpression–mediated growth arrest", Yeast 11:25–32.

Georgopapadakou and Walsh, 1996, "Antifungal agents: chemotherapeutic targets and immunologic strategies", Antimicrob. Agents Chemother. 40:279–291.

Giaever et al., 1999, "Genomic profiling of drug sensitivities via induced haploinsufficiency", Nat. Genet. 21:278–283.

Kunin, 1993, "Resistance to antimicrobial drugs—a worldwide calamity", Ann. Intern. Med. 118:557–561.

Launhardt et al., 1998, "Drug–induced phenotypes provide a tool for the functional analysis of yeast genes", Yeast 14:935–942.

Liu et al., 1992, "Construction of GAL1–regulated yeast cDNA expression library and its application to the identification of genes whose overexpression causes lethality in yeast", Genetics 132:665–673.

Masferrer et al., 1996, "Cyclooxygenase–2 inhibitors: a new class of anti–inflammatory agents that spare the gastrointestinal tract", Gastroenterol. Clin. North Am. 25:363–372.

Mitsuzawa et al., 1989, "Isolation and characterization of temperature–sensitive mutations in the RAS2 and CYR1 genes of Saccharomyces cerevisiae", Genetics 123:739–748.

Neu, 1992, "The crisis in antibiotic resistance", Science 257:1064–1073.

Nishii et al., 1997, "Partial purification of a CAAX–motif–specific protease from bovine brain using a novel fluorometric assay", J. Biochem. 122:402–408.

Rine et al., 1983, "Targeted selection of recombinant clones through gene dosage effects", Proc. Natl. Acad. Sci. USA 80:6750–6754.

Rouse et al., 1995, "Characterization of the katG and inhA genes of isoniazid–resistant clinical isolates of Mycobacterium tuberculosis", Antimicrob. Agents Chemother. 39:2472–2477.

Schimke et al., 1978, "Gene amplification and drug resistance in cultured murine cells", Science 202:1051–1055.

Sharma et al., 1998, "Crystal structure of quinolinic acid phosphoribosyltransferase from Mycobacterium tuberculosis: a potential TB drug target", Structure 6:1587–1599.

Tenover and Hughes, 1996, "The challenges of emerging infectious disease. Development and srpead of multiply–resistant bacterial pathogens", JAMA 275:300–304.

Tomb et al., 1997, "The complete genome sequence of gastric pathogen Helicobacter pylori", Nature 388:539–547.

* cited by examiner

TARGETED METHODS OF DRUG SCREENING USING CO-CULTURE METHODS

This application is a continuation-in-part of U.S. patent application Ser. No. 09/213,120, filed Dec. 15, 1998, now abandoned which in turn is a continuation of International Patent Application Ser. No. PCT/US98/11415 filed Jun. 2, 1998, each of which is incorporated by reference herein in its entirety.

1. FIELD OF THE INVENTION

The present invention relates to methods of screening for molecules, including drugs, that target and inhibit specific proteins or cellular pathways that affect the proliferation, growth or survival of a cell or organism. The methods are based on a co-culture assay, and can be applied to bacteria, yeast, *C. elegans,* and cultured cells, such as mammalian, insect and plant cells.

2. BACKGROUND OF THE INVENTION

2.1. Co-culture Assay

Co-culture experiments have been utilized extensively to identify genes that contribute to the fitness of cells. Giaever et al. (1999, Nat. Genet. 21:278–283) recently showed that from a large pool of cells with distinct genotypes, cells could be identified that had slight differences in fitness when grown in the presence of inhibitors. The genotypes that were responsible for the altered fitness were heterozygous mutations in diploid cells. Thus, this technique was sensitive enough to identify changes in fitness that resulted from the difference between one and two copies of a given gene.

2.2. Identification of Drug Targets

It has been shown that overexpression of a drug's target protein in a cell confers resistance to the cell against the drug. The resistance conferred by overexpression of a target gene has been used as a basis for screening yeast populations transformed with an expression plasmid library for yeast colonies that are resistant to tunicamycin, compactin or ethionine (Rine et al., 1983, Proc. Natl. Acad. Sci. USA 80:6750–6754; Launhardt et al., 1998, Yeast 14:935–942). The ability of a colony to grow after treatment with a drug indicates that the plasmid harbored by the colony directs expression of a protein that confers resistance to the drug, i.e., that the protein is the target of that drug.

2.3. Methods of Drug Discovery

Identification of targets for drug development is a laborious process that has had a low rate of success. Accordingly, there is a need in the art for novel methods for the development of novel drugs and therapies that modulate specific cellular pathways. The present invention provides a method for screening for compounds which specifically inhibit such target pathways. Traditional methods for identifying inhibitors of specific cellular targets typically involve in vitro assays that can directly measure the biochemical activity of an enzyme or the binding of a ligand to a receptor. Alternative methods for identifying inhibitors utilize reporter genes in intact cells that are up- or down-regulated when a specific process has been modulated in the cell by a test compound. While these approaches have been successfully used to identify pharmaceutical lead compounds, they require a considerable amount of lead time and labor to develop prior to screening thousands to hundreds of thousands of chemical compounds or natural products.

Similarly, new antibiotics are desperately needed. The widespread use of antibiotics over the past half century has lead to the emergence of bacterial strains that are resistant to nearly all antibiotics now in use. Thus there is an immediate need to develop fast and efficient methods for producing new antibiotics to combat the increasing number of these antibiotic-resistant strains (Chopra et al., 1997, Antimicrob. Agents Chemother., 37:1563–1571; Cohen, 1992, Science, 257:1050–1055; Kunin, 1993, Ann. Intern. Med., 118:557–561; Neu, 1992, Science, 257:1064–1073; Tenover & Hughes, 1996, JAMA, 275:300–304).

Traditional approaches to antibiotic development have failed to meet these needs. One commonly used approach involves chemical modification of an existing antibiotic to produce a more potent formulation. Another approach involves screening for compounds that target the resistance mechanism of a known antibiotic. Such compounds are then be used in conjunction with the known antibiotic to improve its efficacy. These approaches have been somewhat successful, but are research intensive and such drugs tend to target the same bacterial processes as existing antibiotics, and thus, like the earlier breed of antibiotics, are likely to quickly encounter resistance. A second approach has involved mass screening of compounds for their ability to inhibit bacterial growth. Using microbiological assays, natural products and semisynthetic or synthetic chemicals are screened for their ability to kill or arrest the growth of a target pathogen. At least initially, this approach has the advantage of being simple and relatively inexpensive, and allowing rapid testing of large libraries of compounds. However, the promising lead compounds that emerge from such screens subsequently must be tested for host toxicity. Furthermore, since such screens are result-oriented and blind to mechanism, further studies must be done in order to precisely understand the drug's mechanism of action and to identify its target in the cell.

The genomes of several pathogenic microorganisms, such as *Escherichia coli, Helicobacter pylori,* and *Chlamydia trachomatis,* recently have been sequenced (Blattner et al., 1997, Science 277: 1453; Tomb et al., 1997, Nature, 388: 539–547). The availability of gene sequences encoding all proteins of these bacteria provides an unprecedented opportunity for understanding and manipulating bacterial genomes at the molecular level. A number of genes are known or are suspected to be essential to growth, survival or virulence. Such genes could be ideal targets in screening for novel antibiotics.

The present invention provides screening methods for the identification of drugs or antibiotics that target specific proteins using co-culture methods.

Citation or discussion of a reference herein shall not be construed as an admission that such is prior art to the present invention.

3. SUMMARY OF THE INVENTION

The present invention provides methods for screening for a molecule that inhibits the expression or activity of a protein encoded by a target gene which affects the fitness of a cell. The methods comprise co-culturing a first cell and a second cell, wherein the first cell has higher expression or activity of the protein encoded by the target gene ("target protein") than the second cell, and wherein the first cell further comprises and expresses a reporter gene that is substantially not expressed in said second cell and wherein the first cell and second cell are of the same species and cell type, wherein said target protein affects the fitness of the first cell and second cell, wherein the first cell further comprises and expresses a reporter gene that is substantially not expressed in said second cell, and wherein the first cell and second cell are of the same species and cell type; and measuring the activity or amount of protein encoded by the reporter gene, wherein the activity or amount of protein encoded by the reporter gene is indicative of whether the test molecule inhibits the target gene.

In certain specific embodiments, the first and second cells are selected from the group consisting of a bacterial cell, a yeast cell, an insect cell, a mammalian cell and a plant cell.

In an alternative embodiment, the first and second cells can be groups of cells, e.g., individual multicellular organisms of the same species. In a preferred mode of the embodiment, the species is *C. elegans*.

In one embodiment, the first cell has wild-type levels of target protein expression or activity and the second cell has reduced levels of target protein expression or activity relative to wild type levels of expression or activity. In an alternative embodiment, the first cell has elevated levels of target protein expression or activity relative to wild type levels of expression or activity and the second cell has wild-type levels of target gene expression or activity. In another alternative embodiment, the first cell has elevated levels of target protein expression or activity relative to wild type levels of expression or activity and the second cell has reduced levels of target protein expression or activity relative to wild type levels of expression or activity.

The reduced level of target protein expression or activity can be generated by one copy of the target gene in a diploid cell or mutating the target gene to reduce its activity, by expressing a dominant negative form of a component of a cellular pathway of the target gene, or by lowering the activity or abundance of a target gene encoded RNA. The activity or abundance of a target gene encoded RNA can be lowered, for example, by means of a ribozyme, an anti-sense nucleic acid, a double-stranded RNA or an aptamer.

In a specific embodiment, the elevated level of target gene expression can be generated by recombinantly expressing the target gene from a plasmid or from a chromosome. The elevated level of target gene activity can also be generated by expressing a constitutively active form of the target gene.

In certain embodiments, the reporter gene of the invention encodes an enzyme, a protein or peptide comprising an epitope, a receptor, a transporter, tRNA, rRNA, or a bioluminescent, chemiluminescent or fluorescent molecule. In a specific embodiment, the fluorescent molecule is GFP or a mutant thereof. In a preferred mode of the embodiment, the fluorescent molecule is a mutant GFP having an altered fluorescence wavelength, increased fluorescence, or both. In certain specific embodiment, the mutant GDP is blue GFP. In other modes of the embodiment, the fluorescent molecule is red fluorescent protein or yellow fluorescent protein.

In certain specific embodiments, the first and second cells are co-cultured initially (upon establishment of the co-culture) at a ratio of 1:1, 1:10, 1:100, 1:1000, or 1:10000.

In certain specific embodiments, a screen of the invention is "multiplexed", i.e. one round of screening is used to identify inhibitors of multiple target genes. In such embodiments, screening comprises co-culturing a first cell, and two or more second cells, wherein each said second cell has elevated expression or activity of a different target gene than does the first cell, wherein each target gene positively contributes to the fitness of the first and second cells, wherein said second cells each further comprises and expresses a reporter gene that is substantially not expressed in said first cell, and wherein said first cell and said second cells are of the same species and cell type; exposing the co-culture to a test molecule; and detecting whether a differential sensitivity to the molecule exists between the first cell and one or more of the second cells by detecting an increase in the ratio of cells having reporter gene activity by measuring the activity or amount of protein encoded by the reporter genes in said second cells, wherein said increase in reporter gene activity indicates that the molecule inhibits one or more of said target genes.

In certain modes of multiplexing, the second cells comprise and express the same reporter gene. To determine which of the second cells have increased reporter activity in co-cultures having a significant increase in reporter activity, a secondary round of screening, or a re-screening is carried out. The re-screening can entail polymerase chain reaction (PCR), auxotrophic growth selection, or a co-culture method according to the methods of the present invention. In other modes of multiplexing, the second cells each comprises and expresses a different reporter gene.

In certain specific embodiments, a screen of the invention is used to identify a molecule that inhibits a protein encoded by a first target gene that positively contributes to cell fitness but not the protein encoded by a second, functionally similar target gene. The functionally similar target gene can be a homolog of the target gene from another species, or encode a related protein from the same species. Such related proteins include but are not limited to isozymes, splice variants, or point mutants. Such a method comprises co-culturing a first cell and a second cell, wherein the first cell expresses elevated levels of the target protein and the second cell expresses elevated levels of the protein encoded by the functionally similar gene, wherein said target gene and functionally similar gene both positively contribute to the fitness of the first cell and second cell, wherein the first cell further comprises and expresses a reporter gene that is substantially not expressed in said second cell, and wherein the first cell and second cell are of the same species and cell type; exposing the co-culture to a test molecule; and measuring the activity or amount of protein encoded by the reporter gene, wherein said increase in reporter gene activity indicates that the molecule inhibits the target gene but not the functionally similar gene.

The screening methods of the invention identify compounds that are lead candidates for drugs that cause loss of function of a target gene. There are myriad instances where specific loss of function of a gene is therapeutically desirable, where loss of function results in a desirable phenotype, e.g., in disorders involving low cholesterol levels, cancer, etc. For example, an inhibitor specific to COX2, an oncogene, a cholesterol synthesis enzyme, etc. would be desirable.

The present invention further provides a kit comprising in one or more containers a first cell and a second cell, wherein the first cell has higher expression or activity of the target gene than the second cell, wherein the first cell further comprises and expresses a reporter gene encoding a bioluminescent, chemiluminescent or fluorescent molecule that is substantially not expressed in said second cell and wherein the first cell and second cell are of the same species and cell type.

The present invention further provides an assay system comprising a first cell and a second cell, wherein the first cell has higher expression or activity of the target gene than the second cell, wherein the first cell further comprises and expresses a reporter gene encoding a bioluminescent, chemiluminescent or fluorescent molecule that is substantially not expressed in said second cell and wherein the first cell and second cell are of the same species and cell type.

4. BRIEF DESCRIPTION OF THE FIGURES

Figure 1B:
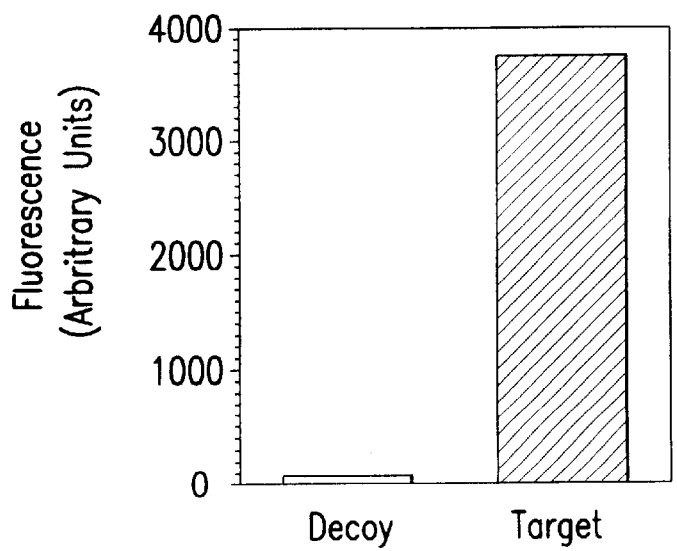

FIG. 1: Fluorescent intensity as a function of decoy: target cell ratio. The experiment was performed in a 96-well plate. Each well contained a total of $1^7$ yeast cells in 0.2 ml medium. The target cells overexpress GFP, whereas the decoy cells harbor a control vector. Fluorescent intensity of the cultures was measured without prior incubation in a Molecular Dynamics Vistra FluorImager. Fluorescence is represented as the average fluorescence units/pixel for each well. The inset shows the fluorescent values for pure cultures ($10^7$ cells) of either the decoy or target yeast cell.

FIG. 2: A Signal to noise ratios of ERG11-target and decoy co-cultures grown in the presence of clotrimazole. Cultures were prepared at various ratios of target: decoy cells (columns). Each ratio was also prepared at various total number of cells per well and are indicated at the top. Clotrimazole, which inhibits the ERG11 gene product, was introduced by serial dilution (rows). The concentrations of clotrimazole are indicated to the left of the table. The volume of medium in each well was 0.225 ml. The plate was allowed to incubate at 30° C. for 88 h. Fluorescence signal was determined by subtracting the fluorescent values from a medium control plate from the fluorescence values of each well in the test plate. Signal to noise ratios were determined by dividing these corrected values with the corresponding values in the no-drug well in the bottom row. B $O.D._{600}$ values of co-cultures in each well after growth. C A fluorescent image of the source plate.

Figure 3:
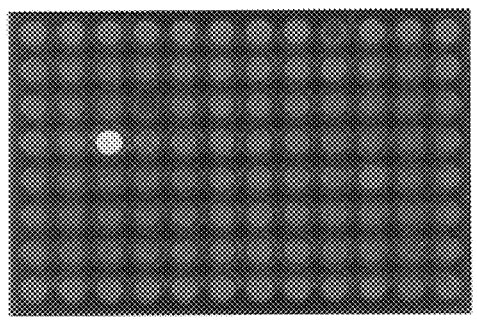
Figure 3:
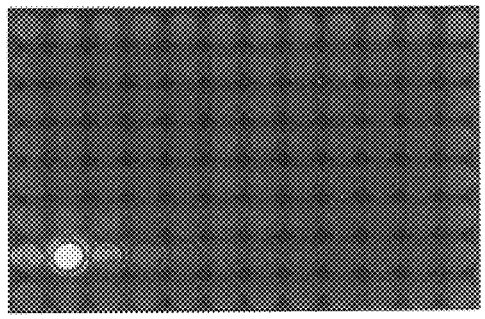
Figure 3:
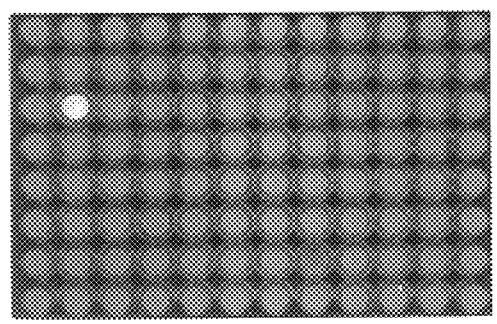
Figure 3:
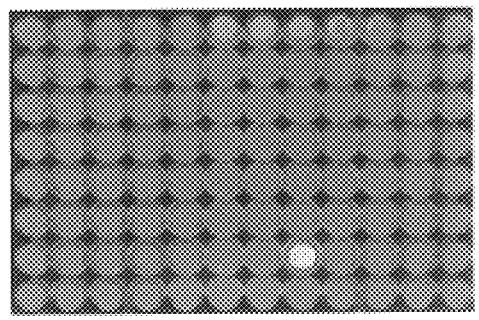

FIG. 3: Results from an ERG11-Target co-culture screen of a chemical library. Target yeast cells overexpressing the ERG11 gene and GFP were mixed with decoy cells at a ratio of 1:1000 and portioned into 96-well plates. Each well contained 25 target cells and 25,000 decoy cells in 0.225 ml YM medium plus 2% casamino acids. 560 generic drugs from the MicroSource™ library were dispensed to each well to a final concentration of 5 μg/ml or 0.5 μg/ml and 1% DMSO. The plates were incubated at 30° C. for ten days. Four representative plates showing four positive hits are shown.

5. DETAILED DESCRIPTION OF THE INVENTION

The present invention provides methods of screening for molecules that inhibit the activity of specific cellular gene products, wherein the inhibition results in either a reduction or an increase in the fitness of the host cell or organism. The methods are based on a co-culture assay, and entail culturing together two cells, i.e., two cell populations, each of which is a population of identical cells, of the same species that differs substantially only in the expression or activity of the gene to be targeted or its encoded protein and the presence or absence of a reporter gene.

In certain specific embodiment, the screen is applied to cultured cells, including but not limited to mammalian and insect cells. In other embodiments, the screen is applied to a multicellular organism such as *C. elegans*. In yet other embodiments, the screens is applied to a unicellular organism. In a preferred embodiment, the unicellular organism is the yeast *Saccharomyces cerevisiae*. In another preferred embodiment, the unicellular organism is a microbe such as a bacterium.

In the co-culture assays of the invention, the gene to be targeted affects the fitness of the cell or organism which is used in the screen. In a specific embodiment, the target gene positively contributes to the fitness of the cell or organism which is used in the screen. The target protein (encoded by the target gene) need not be normally required for fitness, as long as the cell or organism can be manipulated such that the target protein contributes to fitness, preferably becoming essential, for example by mutation of another gene with which the target gene is redundant (see e.g. Section 7, infra). Manipulation of expression of the target gene, either by overexpression or reduction of expression, should not substantially compromise the viability of the cell or organism to be used as a basis for screening. Manipulation sensitizes the host to a molecule which inhibits the target gene or its encoded protein such that the cell or organism comprising the manipulated gene grows at a different rate from the cell or organism comprising the unmanipulated gene in response to exposure to the molecule.

In one specific embodiment, the protein encoded by the target gene positively contributes to the fitness of the cell (e.g., is an essential gene in the cell), and the first cell is initially significantly in the minority in the co-culture (the co-culture is established with a low ratio of first to second cell). An increase in signal indicative of reporter gene activity upon culturing the co-culture in the presence of the test molecule indicates that the molecule inhibits the expression or activity of the target protein.

Accordingly, the methods of the invention provide screens, termed targeted dosage suppression (referred to hereinafter as "TDS") screens, to detect inhibitors of a specific protein. The specific protein is termed the "target protein" and is encoded by the "target gene". The TDS screens provided by the invention can easily be applied for any target gene in any species with a minimal amount of setup time. The only constraint is that the target gene of interest, when inhibited must lead to reduced fitness or growth rate. The TDS screen is applicable for any cell type or organism that has a reasonably short generation time (preferably less than 48 h) and in which gene expression can be modulated. In addition to identifying inhibitory compounds for use as drugs, the methods can be employed to identify proteins or other molecules that inhibit the function of target proteins.

The TDS methods described herein take advantage of both the drug resistance conferred to a cell overexpressing a target gene together with the sensitivity of co-culture (competitive growth) experiments as a means of identifying specific inhibitors.

According to the TDS method of the present invention, one cell expresses higher levels of target protein for which an inhibitor is sought than its co-culture counterpart, or expresses target protein that has higher activity than its co-culture counterpart, or both. One cell is said to overexpress a target protein by virtue of higher expression levels or higher activity of the target protein in the cell. Preferably, the other cell, i.e. the co-culture partner, is isogenic to the overexpressing cell, except for changes relating to expression or activity of a target gene and expression of a reporter gene. As such, the reference point is not wild type expression but expression in the co-culture partner. The rationale for this approach is based on the increased resistance a cell acquires to a particular molecule when the gene encoding the target of the inhibitory molecule is expressed at a higher level or has higher activity in one cell relative to another. For example, the increased expression can result from an increase in the rate of expression of the target gene, an increase in the copy number (gene dosage) of the target gene or a reduction in the rate of expression or copy number of the target gene in the coculture counterpart, or both. In each case, the higher number of target proteins a cell or organism expresses, the more resistant it is to the corresponding inhibitors (Clewell et al., 1975, Proc. Natl. Acad. Sci. USA 72:1720–1724; Schimke et al., 1978, Science 202:1051–1055). Generating a target cell with higher protein activity can alternatively be mediated by expressing an inhibitor of this target protein or a mutant protein in the co-culture partner.

The second component of the TDS method involves mixing the cells overexpressing the target gene (the "target" cell) with an excess of a substantially similar cell (the "decoy" cell) that does not overexpress, or even underexpresses, the target gene. This feature of the screening method utilizes the extraordinary resolving power of co-culture experiments to distinguish between the relative fitness of two cell types. When the target gene positively contributes to fitness of the target cell, and the target and decoy cells are grown in the presence of an inhibitor of the target gene present in the target cell, the target cell will display an increased resistance, or fitness, relative to the decoy cell. During growth of the mixture, the proportion of the target cell relative to the decoy cell will increase until it becomes the predominant, if not sole, member of the population.

As a means of distinguishing the target cell from the decoy cell in cell populations grown in the presence of an inhibitor, the target cell harbors an easily detected marker or reporter gene, such as GFP. Thus, in a preferred embodiment, the target cell expresses both the target gene and GFP at very high levels. The decoy cell does not express GFP. Following culture of the cell mixture in the presence of various modulator candidates, the cells are assessed for fluorescence. Molecules that confer a differential growth advantage to the target cell can easily be detected either with a hand held long wavelength UV light or other equipment that can detect and/or measure fluorescent light.

To insure against false positives resulting from the uncoupling of the reporter gene from the target cell or organism, it is necessary that the genomes of the target and decoy cells do not mix or that the reporter gene is tightly linked (genetically) to overexpression of the target gene. For example, in yeast, this can be achieved by using mating-deficient strains so that the genetic material of the target and decoy cells remains segregated. Alternatively, when the target gene is expressed from a plasmid, the reporter gene is engineered so that is also expressed from the same plasmid. Those of skill in the art can recognize other means of achieving the same result.

In an embodiment wherein the target gene positively contributes to cell fitness, the TDS screen is exquisitely specific since a positive hit indicates that the target gene's expression conferred resistance to the inhibitor candidate. This result would indicate that the chemical was inhibiting the target protein or possibly a functionally related protein or a protein that functions downstream of the target. Over expression of pumps or proteins that degrade the compound could also cause resistance and lead to false positives. However, these cases would be easy to identify because they would be resistant to a large number of different compounds. In some rare instances it is conceivable that the resistance to the inhibitor is conferred by the co-expression of the marker gene. When the marker gene is GFP, this possibility seems unlikely since this protein has not been documented to significantly influence cell physiology.

In another specific embodiment, the protein encoded by the target gene negatively contributes to the fitness of the cell (e.g., its overexpression causes a growth defect such as overexpression lethality), and the first cell is initially significantly in the majority in the co-culture (the co-culture is established with a high ratio of first to second cell). Upon culturing the co-culture in the presence of the test molecule, detection of a fluorescent signal that is at least as high as when the co-culture is initially established, indicates that the molecule inhibits the expression or activity of the target gene's encoded protein (see Section 5.8, infra).

Genetic backgrounds of cells can be manipulated so that a target gene, when overexpressed in the first cell relative to the second cell, either positively or negatively contributes to the fitness of the cell, such that an assay of the invention can be employed.

The TDS screens described herein can be exploited to screen simultaneously for inhibitors of multiple target genes by co-culturing several target cells with the decoy cell, as described in Section 5.9, infra. Section 5.9 also describes variations on the TDS methods for identifying inhibitors of related but not identical target proteins.

In certain embodiments of the present invention, the target gene encodes a protein that is a component of a biological pathway that contributes either positively or negatively to the fitness of a cell. Biological pathways, as used herein, refer to collections of cellular constituents (e.g., protein abundances or activities, protein phosphorylation, RNA species abundances such as mRNA species abundances, or DNA species abundances such as abundances of cDNA species derived from mRNA—as used herein the term "cellular constituent" is not intended to refer to known subcellular organelles such as mitochondria, lysozomes, etc.) which are related in that each cellular constituent in the collection is influenced according to some biological mechanism by one or more other cellular constituents in the collection. In one embodiment, the biological pathway is a signaling or control pathway. Signaling and control pathways typically include primary or intermediate signaling molecules, as well as proteins participating in the signal or control cascades usually characterizing these pathways. In signaling pathways, binding of a signal molecule to a receptor usually directly influences the abundances of intermediate signaling molecules and indirectly influences, e.g., the degree of phosphorylation (or other modification) of pathway proteins. Both of these effects in turn influence activities of cellular proteins that are key effectors of the cellular processes initiated by the signal, for example, by affecting the transcriptional state of the cell. Control pathways, such as those controlling the timing and occurrence of the cell cycle, are similar. Here, multiple, often ongoing, cellular events are temporally coordinated, often with feedback control, to achieve a consistent outcome, such as cell division with chromosome segregation. This coordination is a consequence of functioning of the pathway, often mediated by mutual influences of proteins on each other's degree of phosphorylation or other modification. Other biological pathways having components suitable for use as target proteins include but are not limited to: telomere-related pathways, mating pathways, cell cycle pathways, cell division pathways, cell repair pathways, small molecule synthesis pathways, protein synthesis pathways, DNA synthesis pathways, RNA synthesis pathways, DNA repair pathways, stress-response pathways, cytoskeletal pathways, steroid pathways, receptor-mediated signal transduction pathways, transcriptional pathways, translational pathways, immune response pathways, heat-shock pathways, motility pathways, secretion pathways, endocytotic pathways, protein sorting pathways, phagocytic pathways, photosynthetic pathways, excretion pathways, electrical response pathways, pressure-response pathways, protein modification pathways, small-molecule response pathways, toxic-molecule response pathway transformation pathways, etc. Specifically, the invention herein is illustrated in Section 6 by the erg11 pathway and in Section 7 by the ras cell signaling pathway. Other, well known control pathways suitable for selection of target proteins seek to maintain optimal levels of cellular metabolites in the face of a fluctuating environment. Further examples of cellular pathways operating according to understood mechanisms are well known and will therefore be readily apparent to those of skill in the art.

5.1. Definition and General Techniques

Unless otherwise defined, all technical and scientific terms used herein have the meaning as commonly understood by one of ordinary skill in the art to which this invention belongs. The practice of the present invention employs, unless otherwise indicated, conventional techniques of chemistry, molecular biology, microbiology, recombinant DNA, genetics and immunology. See, e.g., Maniatis et al., 1982, Molecular Cloning, A Laboratory Manual, 2nd ed., Cold Spring Harbor Laboratory, Cold Spring Harbor, N.Y.; Sambrook et al., 1989, Molecular Cloning: A Laboratory Manual (Cold Spring Harbor, N.Y.: Cold Spring Harbor Laboratory Press); Ausubel et al., 1992, Current Protocols in Molecular Biology (New York: John Wiley & Sons); Guthrie & Fink, 1991, Methods Enzymol. 194:1–863.

Fitness of a cell or organism: The growth potential of a specific cell, i.e. the viability or ability of the cell to grow, for example in a competitive growth environment, as preferably measured by the net number of doublings of the cell over a given period of time. Fitness is said to increase when the duration of the cell cycle or occurrence of cell death is reduced. Conversely, fitness is said to be reduced when the duration of the cell cycle or occurrence of cell death increases.

Target gene: a gene for which an inhibitor is sought. The target gene is overexpressed in the target cell and/or underexpressed in the decoy cell. The protein encoded by the target gene is the "target protein".

As used herein, the term "target protein" encompasses functional protein fragments, mutant forms of the protein having higher or lower (but still higher than target protein activity in the decoy cell) activity than the wild type protein (e.g. constitutively active forms of the protein), functionally active muteins, or derivatives of the target protein. The target protein can also be expressed as a fusion protein, e.g. with an epitope tag or with the reporter protein.

As used herein, a "functional fragment" of a protein is any portion of the amino acid sequence that retains a functional activity of the protein, including but not limited to biological activity (e.g., ability to rescue a mutant in the gene encoding the protein).

A polypeptide "mutein" refers to a polypeptide whose sequence contains substitutions, insertions or deletions of one or more amino acids compared to the amino acid sequence of the native or wild type protein. A mutein has at least 50% sequence homology to the wild type protein, preferred is 60% sequence homology, more preferred is 70% sequence homology. Most preferred are muteins having 80%, 90% or 95% sequence homology to the wild type protein, in which sequence homology is measured by any common sequence analysis algorithm, such as Gap or Best-fit.

A "derivative" of a protein refers to polypeptides or fragments thereof that are substantially homologous in primary structural sequence but which include, e.g., in vivo biochemical modifications, including but are not limited to, for example, acetylation, carboxylation, phosphorylation, glycosylation, ubiquitination, various enzymatic modifications, or conservative substitutions, as will be readily appreciated by those well skilled in the art.

The term "fusion protein" refers to polypeptides comprising polypeptides (e.g., fragments or proteins) bound via a peptide bond to heterologous amino acid sequences. Fusion proteins are useful because they can be constructed to contain two or more desired functional elements from two or more different proteins. Fusion proteins can be produced recombinantly by constructing a nucleic acid sequence which encodes the polypeptide or a fragment thereof in frame with a nucleic acid sequence encoding a different protein or peptide and then expressing the fusion protein. cl 5.2. Yeast Methodology In a specific embodiment, S. cerevisiae genes that positively contribute to fitness provide targets for the design or discovery of anti-fungal agents, herbicides and insecticides, and anti-proliferation agents that can be used in a variety of therapeutic, veterinary and agricultural settings.

In one embodiment of the invention, the target gene of the present invention is any gene that positively contributes to the fitness of a cell. In a preferred embodiment, the target gene is an essential gene. The term "essential" refers to a gene that encodes a gene product whose function is required for the fitness, growth or viability of a cell or organism. By way of illustration, the term "essential", when used in reference to S. cerevisiae, can indicate that the gene encodes a product whose function is required for vegetative growth. An illustrative example of a yeast essential gene that can be successfully used as a target gene is erg11, as described in Section 6, infra. The list of known essential genes yeast is growing steadily through the efforts of the yeast genome projects. For example, chromosome VIII essential genes other than erg11 include but are not limited to s10, gpa11, mas2, thr1, ppa1, erg7, gar1, cdc12, msh1, prp8, cdc23, erg9, and sch9 (U. Washington Yeast Genome Project; http://genome.wustl.edu/gsc/yeast/chromosome8ORFs.html). For a complete, updated list of known yeast essential genes, see the Saccharomyces Genome Deletion Project at http://sequence-www.stanford.edu/group/yeast_deletion_project/deletions3.html.

An essential S. cerevisiae gene may be identified by a complete loss-of-function mutation (a knockout) of the gene which prevents yeast vegetative growth on rich medium. However, a complete loss-of-function mutation is not the only way to identify an essential gene in yeast. An essential gene may also be identified by a non-null allele of the gene wherein the non-null allele encodes a protein with a sufficiently reduced biochemical activity that the protein is insufficient to meet the essential function required by the yeast, with the result that yeast vegetative growth is prevented. For example, a non-null allele may be an allele having a point mutation at the active site of an enzyme. Finally, there are a number of genes in yeast that are not essential only because or redundancy or duplication in the genome, such that there are multiple copies of a gene or a family of genes that encode proteins with the same function or overlapping functions. Such genes can be made essential by genetic manipulation, for example by deleting or mutating a redundant or duplicated gene. In illustrative example of a gene that is normally not essential but can be made to do so is rce1, as described in Section 7, infra.

Another category of yeast genes that are useful as target genes according to the methods of the present invention are those that have slow growth phenotypes when deleted. Examples of chromosome VIII slow growth genes include but are not limited to mrp4, myo1, ste12, and eno2 (U. Washington Yeast Genome Project; http://genome.wustl.edu/gsc/yeast/chromosome8ORFs.html).

S. cerevisiae target genes can be used to identify inhibitors of a number of different categories of targets. Target genes of S. cerevisiae that do not have plant and/or mammalian homologs can be used in screening for highly specific anti-fungal agents. Alternatively, S. cerevisiae target genes that have insect or plant homologs can be used in screening for insecticides and herbicides, respectively. Lastly, S. cerevisiae target genes that have mammalian homologs can be used as targets in screening for anti-proliferative agents, such as those that can be used in the treatment of psoriasis, prevention of restenosis after angioplasty and benign and malignant tumors. These groups may not be mutually exclusive. For instance, a S. cerevisiae gene that positively contributes to the fitness of a cell may have a plant homolog but no mammalian homolog. The gene (or the protein it encodes) may be used as a target gene to identify potential anti-fungal agents for mammals as well as a target to isolate herbicides which will be safe to mammals. Similarly, a S. cerevisiae gene may have plant, insect and mammalian homologs, and may be used as a target for the design or discovery of potential herbicides, insecticides and mammalian anti-proliferative agents.

Thus, similarities and differences between S. cerevisiae genes and genes from other organisms can be exploited in the design of a screen. For example, if a target gene is to be useful for identification of anti-fungal agents for human or mammalian use, it preferably does not have a human or non-human mammalian homolog. If a target gene is to be useful for identification of agricultural anti-fungal agents, it is preferable that the gene does not have a plant homolog. If the genes of a mammal or plant do not encode a protein that is homologous to the protein encoded by the S. cerevisiae target gene, inhibitors of the target that are identified by the methods of the present invention have the potential to be highly fungal specific. Alternatively, if the target gene or pathway exhibits some homology with mammalian or plant proteins, screens for new anti-fungal agents according to the methods of the invention may be designed to exploit the differences between the yeast target and the homologous mammalian or plant proteins to produce a specific anti-fungal agent.

The instant invention provides methods to identify novel herbicides and insecticides by screening for molecules that inhibit target genes of S. cerevisiae that are homologous between S. cerevisiae and plants or insects. Such genes not only exhibit sequence similarities but often exhibit functional similarities as well. For example, if a S. cerevisiae gene positively contributes to S. cerevisiae fitness and is homologous to an insect or plant gene there is a reasonable likelihood that the homologous insect or plant gene will be important for growth of the insect or plant as well. Thus, molecules that are identified in screens using S. cerevisiae that has been sensitized by altering genes that are homologous to insect or plant genes and are known to carry out the same function, then that molecule can be used as a insecticide or herbicide. An advantage of this screening method is that insecticides and herbicides designed to interact with certain specific targets may have fewer toxic side effects or be less likely to promote the development of resistance by a pest.

The instant invention provides methods to identify novel anti-proliferation drugs for mammals, especially humans. As discussed above, genes from S. cerevisiae often have homologs in other eukaryotic organisms, including humans. Thus, if the aim of the screen is to identify a molecule for use as a mammalian anti-proliferative agent, the target gene that is sensitized for screening purposes is a homolog of a mammalian gene which is also important for cell proliferation or fitness in mammals. Alternatively, the yeast target gene may be replaced by, or used in combination with, its mammalian counterpart. Targeted anti-proliferation drugs may be more effective than those currently available, or they may be used in conjunction with currently available drugs to inhibit cell proliferation.

Although this embodiment of the invention is exemplified using S. cerevisiae, this method can be practiced using a number of other fungal genera. These include the human pathogens such as Aspergillus, Candida, Neurospora, Cryptococcus, and Trichoderma. In addition, plant pathogens such as Fusarium can be targeted as well. A large number of genes, as well as parts of some of these fungal genomes other than S. cerevisiae, have been cloned and methods of disrupting genes in these fungi are also known.

5.2.1. Methods for the Construction of Mutant Yeast Strains

In several embodiments of the invention, yeast mutations are generated to specifically sensitize a decoy cell to a specific inhibitor molecule. There are a number of methods well known in the art by a gene may be disrupted or mutated in yeast. In one embodiment, an entire gene and create a null allele, in which no portion of the gene is expressed. In other embodiments, a deletion allele may be constructed comprising only a portion of the gene which is not sufficient for gene function, which can be constructed, for example, by inserting a nonsense codon into the sequence of the gene such that translation of the mutant mRNA transcript ends prematurely. Alleles may also be made containing point mutations, individually or in combination, that reduce or abolish gene function. Such methods are well known in the art.

There are a number of different strategies for creating conditional alleles of genes. Broadly, an allele can be conditional for function or expression. An example of an allele that is conditional for function is a temperature sensitive mutation wherein the gene product is functional at one temperature (i.e., permissive temperature) but non-functional at a different temperature (i.e., non-permissive temperature), e.g., due to misfolding or mislocalization. One of ordinary skill in the art can produce mutant alleles which may have only one or a few altered nucleotides but which encode inactive or temperature-sensitive proteins. Temperature-sensitive mutant yeast cells express a functional protein at permissive temperatures but do not express a functional protein at non-permissive temperatures.

An example of an allele that is conditional for expression is a chimeric gene where a regulated promoter controls the expression of the gene. Under one condition the gene is expressed and under another it is not. One may replace or alter the endogenous promoter of the gene with a heterologous or altered promoter that can be activated only under certain conditions. These conditional mutants only express the gene under defined experimental conditions. All of these methods are well known in the art. For example, see Stark, 1998, Methods in Microbiology 26:83–100; Garfinkel et al., 1998, Methods in Microbiology 26:101–118; and Lawrence & Rothstein, 1991, Methods in Enzymology 194:281–301.

In another embodiment of the invention, a gene may have decreased expression without disrupting or mutating the gene. For instance, the expression of gene may be decreased by transforming yeast with an antisense molecule under the control of a regulated or constitutive promoter (see Nasr et al., 1995, Molecular & General Genetics 249:51–57). Such an antisense construct operably linked to an inducible promoter and introduced into S. cerevisiae to study the function of a conditional allele (see Nasr et al. supra), or to act as a perturbations of a cell.

Gene expression may also be decreased by inserting a sequence by homologous recombination into or next to the gene of interest wherein the sequence targets the mRNA or the protein for degradation. For instance, one can introduce a construct that encodes ubiquitin such that a ubiquitin fusion protein is produced. This protein will be likely to have a shorter half-life than the wild type protein. See, e.g., Johnson et al., 1992, EMBO J. 11:497–505.

In a preferred mode, a target gene is completely disrupted in order to ensure that there is no residual function of the gene. One can disrupt a gene by "classical" or PCR-based methods. The "classical" method of gene knockout is described by Rothstein, 1991. However, in some embodiments, it is preferable to use a PCR-based deletion method because it is faster and less labor intensive.

5.2.2. Yeast Expression Systems

The present invention provides yeast cells that overexpress a target gene by recombinant means for use as a target cell in the TDS screen. The invention also provides yeast cells that underexpress a target gene for use as a decoy cell in the TDS screen.

In a preferred embodiment, the target gene is overexpressed in an inducible manner so that levels of gene expression can be modulated. Any of the several known controllable expression systems available for use in the budding yeast Saccharomyces cerevisiae are adaptable to this invention (Mumberg et al., 1994, Nucl. Acids Res. 22:5767–5768). Usually, gene expression is controlled by transcriptional controls, with the promoter of the gene to be controlled replaced on its chromosome by a controllable, exogenous promoter. The most commonly used controllable promoter in yeast is the GAL1 promoter (Johnston et al., 1984, Mol Cell. Biol. 8:1440–1448). The GAL1 promoter is strongly repressed by the presence of glucose in the growth medium, and is gradually switched on in a graded manner to high levels of expression by the decreasing abundance of glucose and the presence of galactose. The GAL1 promoter usually allows a 5–100 fold range of expression control on a gene of interest.

Other frequently used promoter systems include the MET25 promoter (Kejan et al., 1986, Nucl. Acids. Res. 14:7861–7871), which is induced by the absence of methionine in the growth medium, the CUP1 promoter, which is induced by copper (Mascorro-Gallardo et al., 1996, Gene 172:169–170), the CYC1 promoter, which is repressed in the presence of glucose (Guarente and Ptashne, 1981, Proc. Natl. Acad. Sci. USA 78:2199–2203) and PHO5 which can be regulated by thiamine (Meyhack et al., 1982, EMBO J. 1:675–680). All of these promoter systems are controllable in that gene expression can be incrementally controlled by incremental changes in the abundances of a controlling moiety in the growth medium.

One disadvantage of the above listed expression systems is that control of promoter activity (effected by, e.g., changes in carbon source, removal of certain amino acids), often causes other changes in cellular physiology which independently alter the expression levels of other genes. A recently developed system for yeast, the Tet system, alleviates this problem to a large extent (Gari et al., 1997, Yeast 13:837–848). The Tet promoter, adopted from mammalian expression systems (Gossen et al., 1995, Proc. Nat. Acad. Sci. USA 89:5547–5551) is modulated by the concentration of the antibiotic tetracycline or the structurally related compound doxycycline. Thus, in the absence of doxycycline, the promoter induces a high level of expression, and the addition of increasing levels of doxycycline causes increased repression of promoter activity. Intermediate levels gene expression can be achieved in the steady state by addition of intermediate levels of drug. Furthermore, levels of doxycycline that give maximal repression of promoter activity (10 micrograms/ml) have no significant effect on the growth rate on wild type yeast cells (Gari et al., 1997, Yeast 13:837–848).

In an alternative embodiment, the target gene is overexpressed under the control of a constitutive promoter. Suitable constitutive promoters include but are not limited to promoters of the PGK genes (3-phosphoglycerate kinase; Hitzeman et al., 1983, Science 219:620–625), TDH genes encoding GAPDH (Glyceraldehyde phosphate dehydrogenase; Holland and Holland, 1979, J. Biol. Chem. 254:9839–9845), TEF1 genes (Elongation factor 1; Cottrelle et al., 1985, J. Biol. Chem. 260:3090–3096), and MFα1 (αsex pheromone precursor; Inokuchi et al., 1987, Mol. Cell. Biol. 7:3185–3193).

The reporter gene for marking the target cell is also expressed by the methods described in this section.

In a certain specific embodiment, expression systems such as the ones described above, are introduced for use into cells or organisms lacking the corresponding endogenous gene and/or gene activity, e.g., cells in which the endogenous gene has been disrupted or deleted. The recombinant gene can be used to express a mutant target protein or fragment thereof that has reduced activity to generate a decoy cell or a target protein or functional fragment thereof having wild type or increased activity to generate a target cell. Examples of classes of protein mutants having increased or reduced activity are described in Section 5.2.4., infra.

5.2.3. Methods of Modifying Protein Abundance

The present invention provides yeast target cells with increased target protein abundance and yeast decoy cells with reduced target protein abundance.

Methods of altering protein abundances include, inter alia, those altering protein degradation rates and those using antibodies (which bind to proteins affecting abundances of activities of native target protein species). Increasing (or decreasing) the degradation rates of a protein species decreases (or increases) the abundance of that species. Methods for controllably increasing the degradation rate of a target protein in response to elevated temperature and/or exposure to a particular drug, which are known in the art, can be employed in this invention. For example, one such method employs a heat-inducible or drug-inducible N-terminal degron, which is an N-terminal protein fragment that exposes a degradation signal promoting rapid protein degradation at a higher temperature (e.g., 37° C.) and which is hidden to prevent rapid degradation at a lower temperature (e.g., 23° C.) (Dohmen et al., 1994, Science 263:1273–1276). Such an exemplary degron is Arg-DHFR$^{ts}$, a variant of murine dihydrofolate reductase in which the N-terminal Val is replaced by Arg and the Pro at position 66 is replaced with Leu. According to this method, for example, a gene for a target protein, P, is replaced by standard gene targeting methods known in the art (Lodish et al., 1995, Molecular Biology of the Cell, Chpt. 8, New York: W.H. Freeman and Co.) with a gene coding for the fusion protein Ub-Arg-DHFR$^{ts}$-P ("Ub" stands for ubiquitin). The N-terminal ubiquitin is rapidly cleaved after translation exposing the N-terminal degron. At lower temperatures, lysines internal to Arg-DHFR$^{ts}$ are not exposed, ubiquitination of the fusion protein does not occur, degradation is slow, and active target protein levels are high. At higher temperatures (in the absence of methotrexate), lysines internal to Arg-DHFR$^{ts}$ are exposed, ubiquitination of the fusion protein occurs, degradation is rapid, and active target protein levels are low. Heat activation of degradation is controllably blocked by exposure methotrexate. This method is adaptable to other N-terminal degrons which are responsive to other inducing factors, such as drugs and temperature changes.

Target protein abundances and also, directly or indirectly, their activities can also be decreased by neutralizing antibodies or increased by activating antibodies.

Antibodies can be introduced into cells in numerous fashions. In a preferred embodiment, an antibody is introduced into a cell by transforming hybridoma mRNA encoding the antibody into the cell (Burke et al., 1984, Cell 36:847–858). In a further technique, recombinant antibodies can be engineering and ectopically expressed in a wide variety of non-lymphoid cell types to bind to target proteins as well as to block target protein activities (Biocca et al., 1995, Trends in Cell Biology 5:248–252). Preferably, expression of the antibody is under control of a controllable promoter, such as the Tet promoter. A first step is the selection of a particular monoclonal antibody with appropriate specificity to the target protein (see below). Then sequences encoding the variable regions of the selected antibody can be cloned into various engineered antibody formats, including, for example, whole antibody (immunoglobulin), Fab fragments, Fv fragments, single chain Fv fragments ($V_H$ and $V_L$ regions united by a peptide linker) ("ScFv" fragments), diabodies (two associated ScFv fragments with different specificities), and so forth (Hayden et al., 1997, Current Opinion in Immunology 9:210–212). Intracellularly expressed antibodies of the various formats can be targeted into cellular compartments (e.g., the cytoplasm, the nucleus, the mitochondria, etc.) by expressing them as fusions with the various known intracellular leader sequences (Bradbury et al., 1995, Antibody Engineering, vol. 2, Borrebaeck ed., IRL Press, pp 295–361). In particular, the ScFv format appears to be particularly suitable for cytoplasmic targeting.

For preparation of monoclonal antibodies directed towards a target protein, any technique that provides for the production of antibody molecules by continuous cell lines in culture may be used. Such techniques include, but are not restricted to, the hybridoma technique originally developed by Kohler and Milstein (1975, Nature 256:495–497), the trioma technique, the human B-cell hybridoma technique (Kozbor et al., 1983, Immunology Today 4:72), and the EBV hybridoma technique to produce human monoclonal antibodies (Cole et al., 1985, in Monoclonal Antibodies and Cancer Therapy, Alan R. Liss, Inc., pp. 77–96). According to the invention, human antibodies may be used and can be obtained by using human hybridomas (Cote et al., 1983, Proc. Natl. Acad. Sci. U.S.A. 80:2026–2030), or by transforming human B cells with EBV virus in vitro (Cole et al., 1985, in Monoclonal Antibodies and Cancer Therapy, Alan R. Liss, Inc., pp. 77–96). In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for the target protein together with genes from a human antibody molecule of appropriate biological activity can be used; such antibodies are within the scope of this invention. Humanized antibodies with the complementarity determining regions (CDRs) of a mouse antibody, and human framework regions can also be used.

Additionally, where monoclonal antibodies are advantageous, they can be alternatively selected from large antibody libraries using the techniques of phage display (Marks et al., 1992, J. Biol. Chem. 267:16007–16010). Using this technique, libraries of up to $10^{12}$ different antibodies have been expressed on the surface of fd filamentous phage, creating a "single pot" in vitro immune system of antibodies available for the selection of monoclonal antibodies (Griffiths et al., 1994, EMBO J. 13:3245–3260). Selection of antibodies from such libraries can be done by techniques known in the art, including contacting the phage to immobilized target protein, selecting and cloning phage bound to the target, and subcloning the sequences encoding the antibody variable regions into an appropriate vector expressing a desired antibody format.

According to the invention, techniques described for the production of single chain antibodies (U.S. Pat. Nos. 4,946,778 and 5,359,046) can be adapted to produce single chain antibodies specific to the target protein. An additional embodiment of the invention utilizes the techniques described for the construction of Fab expression libraries (Huse et al., 1989, Science 246:1275–1281) to allow rapid and easy identification of monoclonal Fab fragments with the desired specificity for the target protein.

In the production of antibodies, screening for the desired antibody can be accomplished by techniques known in the art, e.g., ELISA (enzyme-linked immunosorbent assay). To select antibodies specific to a target protein, one may assay generated hybridomas or a phage display antibody library for an antibody that binds to the target protein.

5.2.4. Methods of Modifying Protein Activity

The present invention provides yeast target cells with increased target protein activity and yeast decoy cells with reduced target protein activity.

Methods of directly modifying protein activities include, inter alia, mutations, e.g., temperature-sensitive mutations, dominant negative mutations, gain of function mutations, e.g., those that give rise to constitutively active proteins, specific drugs the addition of chemical moieties such as phosphate or acetyl groups, or amino acid substitutions that mimic the addition of such chemical moieties, and the use of antibodies.

Dominant negative mutations are mutations to endogenous genes or mutant recombinant genes that when expressed in a cell disrupt the activity of a targeted protein species. Depending on the structure and activity of the targeted protein, general rules exist that guide the selection of an appropriate strategy for constructing dominant negative mutations that disrupt activity of that target (Hershkowitz, 1987, Nature 329:219–222). In the case of active monomeric forms, overexpression of an inactive form can cause competition for natural substrates or ligands sufficient to significantly reduce net activity of the target protein. Such overexpression can be achieved by, for example, associating a promoter, preferably a controllable or inducible promoter, of increased activity with the mutant gene. Alternatively, changes to active site residues can be made so that a virtually irreversible association occurs with the target ligand. Such can be achieved with certain tyrosine kinases by careful replacement of active site serine residues (Perlmutter et al., 1996, Current Opinion in Immunology 8:285–290).

In the case of active multimeric forms, several strategies can guide selection of a dominant negative mutant. Multimeric activity can be controllably decreased by expression of genes coding exogenous protein fragments that bind to multimeric association domains and prevent multimer formation. Alternatively, controllable over expression of an inactive protein unit of a particular type can tie up wild-type active units in inactive multimers, and thereby decrease multimeric activity (Nocka et al., 1990, EMBO J. 9:1805–1813). For example, in the case of dimeric DNA binding proteins, the DNA binding domain can be deleted from the DNA binding unit, or the activation domain deleted from the activation unit. Also, in this case, the DNA binding domain unit can be expressed without the domain causing association with the activation unit. Thereby, DNA binding sites are tied up without any possible activation of expression. In the case where a particular type of unit normally undergoes a conformational change during activity, expression of a rigid unit can inactivate resultant complexes. For a further example, proteins involved in cellular mechanisms, such as cellular motility, the mitotic process, cellular architecture, and so forth, are typically composed of associations of many subunits of a few types. These structures are often highly sensitive to disruption by inclusion of a few monomeric units with structural defects. Such mutant monomers disrupt the relevant protein activities and can be controllably expressed in a cell.

In addition to dominant negative mutations, mutant target proteins that are sensitive to temperature (or other exogenous factors) or constitutively active can be found by mutagenesis and screening procedures that are well-known in the art.

Also, one of skill in the art will appreciate that expression of antibodies binding and inhibiting a target protein can be employed as another dominant negative strategy.

5.3. Mammalian and Insect Cell Methodology

The TDS screens of the invention can also be used with cultured mammalian and insect cells. Genes of cultured cells that positively contribute to fitness can provide targets for the design or discovery of anti-proliferation and anti-tumor drugs, antiviral drugs and insecticides that can be used in a variety or therapeutic, veterinary and agricultural settings.

Genes that positively contribute to fitness of cultured mammalian cells, including but not limited to essential genes, can be used as targets in screening for anti-proliferative agents, such as those that can be used in the treatment of psoriasis, prevention of restenosis, after angioplasty and benign and malignant tumors, for example. Cultured mammalian cells can also be used to screen for drugs to treat human disorders or diseases if a target gene can be identified (a) whose overactivity or abnormal activity contributes to the disease or disorder, and (b) the fitness of a cultured cell can be made dependent on the activity of said target gene.

Genes that positively contribute to fitness of cultured insect cells, including but not limited to essential genes, can be used to identify inhibitors of two useful classes of targets.

Target genes that are not conserved between insects and mammals or that have no mammalian homologs can be used as targets in screening for insecticides. Conversely, target insect genes that have conserved mammalian homologs can be used to screen for anti-proliferative agents, as described for cultured mammalian cells.

The present invention provides mammalian and insect cells in which the target gene of choice is underexpressed for use as a decoy cell in the TDS screen. Such underexpression refers to a reduced level of expression or activity in one cell or organism relative to a co-culture partner. Underexpression can be achieved by lowering the levels of RNA encoding a target protein or by lowering the levels of activity of the target protein itself, as is described below.

5.3.1. Methods of reducing RNA Abundance or Activity

Underexpression in tissue culture is best achieved by reducing the abundancy or activity of the mRNA encoding the target protein. Methods of reducing RNA abundances and activities currently fall within three classes, ribozymes, antisense species, and RNA aptamers (Good et al., 1997, Gene Therapy 4:45–54). Controllable exposure of a cell to these entities permits controllable perturbation of RNA abundances.

Ribozymes are RNAs which are capable of catalyzing RNA cleavage reactions. (Cech, 1987, Science 236:1532–1539; PCT International Publication WO 90/11364, published Oct. 4, 1990; Sarver et al., 1990, Science 247:1222–1225). "Hairpin" and "hammerhead" RNA ribozymes can be designed to specifically cleave a particular target mRNA. Rules have been established for the design of short RNA molecules with ribozyme activity, which are capable of cleaving other RNA molecules in a highly sequence specific way and can be targeted to virtually all kinds of RNA. (Haseloff et al., 1988, Nature 334:585–591; Koizumi et al., 1988, FEBS Lett. 228:228–230; Koizumi et al., 1988, FEBS Lett. 239:285–288). Ribozyme methods for underexpression of a target gene involve inducing expression in a cell, etc. of such small RNA ribozyme molecules. (Grassi and Marini, 1996, Annals of Medicine 28:499–510; Gibson, 1996, Cancer and Metastasis Reviews 15:287–299).

Ribozymes can be routinely expressed in vivo in sufficient number to be catalytically effective in cleaving mRNA, and thereby modifying mRNA abundances in a cell. (Cotten et al., 1989, EMBO J. 8:3861–3866). In particular, a ribozyme coding DNA sequence, designed according to the previous rules and synthesized, for example, by standard phosphoramidite chemistry, can be ligated into a restriction enzyme site in the anticodon stem and loop of a gene encoding a tRNA, which can then be transformed into and expressed in a cell of interest by methods routine in the art. Preferably, an inducible promoter (e.g., a glucocorticoid or a tetracycline response element) is also introduced into this construct so that ribozyme expression can be selectively controlled. tDNA genes (i.e., genes encoding tRNAs) are useful in this application because of their small size, high rate of transcription, and ubiquitous expression in different kinds of tissues. Therefore, ribozymes can be routinely designed to cleave virtually any mRNA sequence, and a cell can be routinely transformed with DNA coding for such ribozyme sequences such that a controllable and catalytically effective amount of the ribozyme is expressed. Accordingly the abundance of virtually any RNA species in a cell can be perturbed.

In another embodiment, activity of a target RNA (preferable mRNA) species, specifically its rate of translation, can be controllably inhibited by the controllable application of antisense nucleic acids. An "antisense" nucleic acid as used herein refers to a nucleic acid capable of hybridizing to a sequence-specific (e.g., non-poly A) portion of the target RNA, for example its translation initiation region, by virtue of some sequence complementarity to a coding and/or non-coding region. The antisense nucleic acids of the invention are produced intracellularly by transcription of exogenous, introduced sequences in controllable quantities sufficient to perturb translation of the target RNA.

Preferably, antisense nucleic acids are of at least six nucleotides and to about 200 oligonucleotides). The antisense nucleic acids of the invention comprise a sequence complementary to at least a portion of a target RNA species. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a target RNA it may contain and still form a stable duplex (or triplex, as the case may be). One skilled in the art can ascertain a tolerable degree of mismatch by use of standard procedures to determine the melting point of the hybridized complex. The amount of antisense nucleic acid that will be effective in the inhibiting translation of the target RNA can be determined by standard assay techniques.

The antisense nucleic acids of the invention are controllably expressed intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian and insect cells. Expression of the sequences encoding the antisense RNAs can be by any promoter known in the art to act in a cell of interest. Such promoters can be inducible or constitutive. Most preferably, promoters are controllable or inducible by the administration of an exogenous moiety in order to achieve controlled expression of the antisense oligonucleotide. Such controllable promoters include but are not limited to the Tet promoter, the SV40 early promoter region (Bemoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc.

Therefore, antisense nucleic acids can be designed to target virtually any mRNA sequence, and a cell can be routinely transformed with nucleic acids coding for such antisense sequences such that an effective and controllable amount of the antisense nucleic acid is expressed. Accordingly the translation of virtually any RNA species in a cell can be controllably perturbed.

Finally, in a further embodiment, RNA aptamers can be introduced into or expressed in a cell. RNA aptamers are specific RNA ligands for proteins, such as for Tat and Rev RNA (Good et al., 1997, Gene Therapy 4:45–54) that can specifically inhibit their translation.

5.3.2. Methods of Modifying Protein Abundance

The present invention provides cultured mammalian and insect target cells with increased target protein abundance and cultured mammalian and insect decoy cells with reduced target protein abundance. Methods for modifying target protein abundance in cultured mammalian or insect cells are achieved essentially as described for yeast in Section 5.2.3., supra.

For lowering protein abundance in cultural mammalian and insect cells using an N-terminal degron, care is taken in the selection of the degron to ensure that it is functional at a temperature compatible with the growth of the cell.

5.3.3. Methods of Modifying Protein Activities

The present invention provides cultured mammalian and insect target cells with increased target protein activity and cultured mammalian and insect decoy cells with reduced target protein activity. Methods for modifying target protein activity in cultured mammalian or insect cells are achieved essentially as described for yeast in Section 5.2.4., supra.

5.3.4. Cell Culture Overexpression Systems

In cultured mammalian and insect cells, several means of overexpression of genes are available (Spencer, 1996, Trends Genet. 12:181–187). By way of example, as mentioned in Section 5.2.2 above, the Tet system is widely used, both in its original form, the "forward" system, in which addition of doxycycline represses transcription, and in the newer "reverse" system, in which doxycycline addition stimulates transcription (Gossen et al., 1995, Proc. Natl. Acad. Sci. USA 89:5547–5551; Hoffmann et al., 1997, Nucl. Acids. Res. 25:1078–1079; Hoffmann et al., 1996, Proc. Natl. Acad. Sci. USA 83:5185–5190; Paulus et al., 1996, Journal of Virology 70:62–67). Another commonly used controllable promoter system in mammalian cells is the ecdysone-inducible system developed by Evans and colleagues (No et al., 1996, Proc. Nat. Acad. Sci. USA 93:3346–3351), where expression is controlled by the level of muristerone added to the cultured cells. Also, expression can be modulated using the "chemical-induced dimerization" (CID) system developed by Schreiber, Crabtree, and colleagues (Belshaw et al., 1996, Proc. Nat. Acad. Sci. USA 93:4604–4607; Spencer, 1996, Trends Genet. 12:181–187) and similar systems of controllable gene expression, such as those originally developed in yeast. In this system, the gene of interest is put under the control of the CID-responsive promoter, and transfected into cells expressing two different hybrid proteins, one comprised of a DNA-binding domain fused to FKBP12, which binds FK506. The other hybrid protein contains a transcriptional activation domain also fused to FKBP12. The CID inducing molecule is FK1012, a homodimeric version of FK506 that is able to bind simultaneously both the DNA binding and transcriptional activating hybrid proteins. In the graded presence of FK1012, graded transcription of the controlled gene is activated.

For other modes of constitutive or inducible expression, promoters that can be used include but are not limited to any of the following promoters: to, the SV40 early promoter region (Benoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), and the regulatory sequence of the immediate-early gene of human cytomegalovirus (Foecking, M. and Hofstetter, H., 1986, Gene 45:101–105; U.S. Pat. No. 5,168,062).

For each of the cell culture expression systems described above, as is widely known to those of skill in the art, the target gene is placed under the control of the promoter of choice, and a plasmid harboring this construct along with an antibiotic resistance gene is transfected into cultured mammalian or insect cells. In general, the plasmid DNA integrates into the genome, and drug resistant colonies are selected and screened for appropriate expression of the regulated gene. Alternatively, the regulated gene can be inserted into an episomal plasmid such as pCEP4 (Invitrogen, Inc.), which contains components of the Epstein-Barr virus necessary for plasmid replication.

In a preferred embodiment, a reporter gene operably linked to a promoter is present on the plasmid harboring the target gene. To generate a decoy cell, a similar plasmid harboring no target gene insert or having a mutant promoter can be used.

5.4. C. Elegans Methodology

The present invention provides C. elegans strains which may be used in the identification and characterization of molecules that inhibit genes that contribute positively or negatively to cell and/or organism fitness, according to the methods of the present invention. Such C. elegans are characterized by elevated levels of target protein expression or activity in a target warm relative to a decoy worm.

C. elegans genes that contribute to fitness can be used to identify anti-proliferative agents for use in the treatment of mammalian diseases or disorders of hyperproliferation if the genes have conserved mammalian homologs. Such genes may also be used to screen for drugs to treat other mammalian including human, disorders or diseases if the genes (a) are known to contribute to a disease by overactivity or abnormal expression, and (b) the fitness of a worm-strain can be made to be dependent on the activity of the genes. For example, if the gene does not contribute to the fitness of a mild type worm, a worm strain with a mutation in a functionally redundant gene can be generated for use in a TDS screen.

Elevated levels of target gene expression can be overexpression of the target gene in the target worm, underexpression (e.g., due to inactivation) of the target gene in the decoy worm expression of the target at a developmental time different from wild-type animals, in a decoy strain, for example, loss of expression of the target gene at a time when the target gene is necessary for cellular fitness.

The present invention provides genetically-engineered nematodes as target and/or decoy strains. The strains may harbor: (a) a deletion or insertion in the target gene; (b) interfering RNAs derived from a target gene; and/or (c) transgenes for expression of wild-type or mutant forms of such genes, as described above.

In a specific embodiment in one type of strain, a nucleic acid has been recombinantly introduced into the genome of the worm as an additional gene, under the regulation of either an exogenous or an endogenous promoter element, and as either a minigene or a large genomic fragment. The nucleic acid can encode a titratable suppressor or dominant negative mutant of the target gene for the generation of a decoy strain for the TDS screen. Conversely, the nucleic acid can encode a wild type target protein for overexpression to generate a target strain for a TDS screen.

It is preferable to ensure that the expression of the target gene is manipulated in all tissues since the growth modulation caused by a test compound can be mediated through a specific cell type or tissue.

The invention further provides animals with mutated or inactivated genes, e.g. produced by chemicals or x-ray mutagenesis, to use as decoy strains in TDS screens.

C. elegans, like many nematodes, is hermaphroditic. Their reproduction takes place from the fertilization of oocytes by sperm that usually arise from the same individual. Nevertheless, when the target and decoy worm lines are mixed and allowed to propagate, sexual reproduction between the two worm lines will take place. The target and decoy lineages preferably are isogenic but for the target and reporter genes, but can be any two lineages that are substantially different only in the activity of expression of a target gene or protein encoded by the target gene, and the presence or absence of a reporter gene. Therefore, the segregation pattern of a minichromosome or transgene is not important, as long as the reporter gene is genetically linked to the target gene. The only critical components for the success of a TDS screen in a whole animal are: 1) the ability of the target gene to confer sensitivity to a specific compound in the target animal; and 2) the ease and reliability of reporter gene for detection. That two factors can be assessed in a pilot screen prior to carrying out a large scale screen, for example by identifying suitable screening conditions using a control molecule, such as a known inhibitor of the target gene.

Methods for the creation of C. elegans strains having elevated target gene expression in the target worm relative to the decoy worm are described below. Expression modification methods include any method known to one skilled in the art. Specific examples include but are not limited to EMS chemical mutagenesis, Tc1 transposon mutagenesis, double-stranded RNA interference, and transgene-mediated mis-expression. In the creation of transgenic animals, it is preferred that heterologous (i.e., non-native) promoters be used to drive transgene expression.

For screening purposes, test compounds can be introduced into nematodes by diffusion, ingestion, microinjection, or shooting with a particle gun. In a preferred embodiment, the test compound is spread on the worm medium for ingestion.

5.4.1. EMS Chemical Deletion Mutagenesis

The present invention provides a decoy worm having reduced target gene activity, preferably to increase the sensitivity of a TDS screen when the target worm has target gene or target gene-encoded protein or activity that is elevated relative to wild type expression or activity. In a specific embodiment, such decoy strains comprise mutated target genes. In a specific embodiment, chemical deletion mutagenesis is used to generate reduced expression of a target gene in C. elegans. In a preferred embodiment, the chemical mutagen is ethyl methanesulfonate (EMS). A decoy strain can be heterozygous for an EMS deletion mutant that is a null allele of the target gene, or heterozygous or homozygous for an EMS deletion mutant that is a partial loss of function allele, i.e., a hypomorph, of the target gene.

EMS is a commonly-used chemical mutagen for creating loss-of-function mutations in genes-of-interest in *C. elegans*. Approximately 13% of mutations induced by EMS are small deletions. With the methods described in this section, there is approximately a 95% probability of identifying a deletion-of-interest by screening $4 \times 10^6$ EMS-mutagenized genomes. Briefly, this procedure involves creating a library of several million mutagenized *C. elegans* which are distributed in small pools in 96-well plates, each pool composed of approximately 400 haploid genomes. A portion of each pool is used to generate a corresponding library of genomic DNA derived from the mutagenized nematodes. The DNA library is screened with a PCR assay to identify pools that carry genomes with deletions-of-interest, and mutant worms carrying the desired deletions are recovered from the corresponding pools of the mutagenized animals. Although EMS is a preferred mutagen to generate deletions, other mutagens can be used that also provide a significant yield of deletions, such as X-rays, gamma-rays, diepoxybutane, formaldehyde and trimethylpsoralen with ultraviolet light.

Nematodes may be mutagenized with EMS using any procedure known to one skilled in the art, such as the procedure described by Sulston and Hodgkin (1988, Methods, pp. 587–606, in The Nematode *Caenorhabditis elegans*, Wood, Ed., Cold Spring Harbor Laboratory Press, Cold Spring Harbor, N.Y.). By way of example, following exposure to the mutagen, nematodes are dispensed into petri dishes, incubated one to two days, and embryos isolated by hypochlorite treatment (Id.) Embryos are allowed to hatch and L1 larvae are collected following overnight incubation. The larvae are distributed in petri plates at an average density of 200 animals per plate and incubated for 5 to 7 days until just starved. A sample of nematodes is collected from each plate by washing with a solution of distilled water, and the nematodes washed from each plate are placed in one well of a 96-well plate. Worms are lysed by addition of an equal volume of lysis buffer (100 mM KCl, 20 mM Tris-HCl pH 8.3, 5 mM $MgCl_2$, 0.9% Nonidet P-40, 0.9% Tween-20, 0.02% gelatin, and 400 µg/ml proteinase K) followed by incubation at –80° C. for 15 minutes, 60° C. for 3 hours, and 95° C. for 15–30 minutes. The DNA-containing lysates are kept by storage of plates at –80° C. until analyzed further. Live nematodes from each plate are aliquoted into tubes within racks for storage at –80° C., such that the physical arrangement of tubes of live animals is the same as the arrangement of corresponding DNA lysates in the 96-well plates.

Further by way of example, a pooling strategy is then used to allow efficient PCR screening of the DNA lysates. The pools are made from each 96-well plate by mixing 10 µl of lysate from 8 wells comprising each column of wells in a plate. The pooled lysates for each column are used for screening with PCR. PCR primers are designed for each locus-of-interest to be about 1.5 to 12 kb apart, depending on the size of the locus, such that deletions encompassing the entire coding regions of target genes can be detected following a previously-described procedure (see Plasterk, 1995, Methods in Cell Biology 48:59–80). For each region, two sets of primer pairs are chosen for carrying out a nested PCR strategy such that an outside set is used for the first round of PCR and an inside set is used for the second round of PCR. The second round of PCR is performed to achieve greater specificity in the reaction. Products of the second round of PCR can be analyzed by electrophoresis in 1% agarose gels to determine if a potential deletion product has been generated.

5.4.2. Tc1 Transposon Insertion Mutagenesis

Reduction of target gene expression in *C. elegans* can alternatively be achieved by mutagenesis using the transposable element Tc1. Insertion of the transposable element into a target gene can result in the inactivation of target gene function. Starting with a strain that contains a high copy number of the Tc1 transposable element in a mutator background (i.e., a strain in which the transposable element is highly mobile), a Tc1 library containing approximately 3,000 individual cultures is created as previously described (Id.). The library is screened for Tc1 insertions in the region of interest using the polymerase chain reaction with one set of primers specific for Tc1 sequence and one set of gene-specific primers. Because Tc1 exhibits a preference for insertion within introns, it is sometimes necessary to carry out a secondary screen of populations of insertion animals for imprecise excision of the transposable element, which can result in deletion of part or all of the gene of interest (generally, 1–2 kb of genomic sequence is deleted). The screen for Tc1 deletions is performed and deletion animals are recovered in the same manner as for the EMS screen described above.

5.4.3. Double-stranded RNA Interference

A *C. elegans* strain that underexpresses a target gene can be generated using a method based on the interfering properties of double-stranded RNAs derived from the coding regions of the identified genes (see Fire et al., 1998, Nature 391:806–811). In this method, sense and antisense RNAs derived from a substantial portion of a *C. elegans* target gene are synthesized in vitro from phagemid DNA templates containing cDNA clones of target genes which are inserted between opposing promoters for T3 and T7 phage RNA polymerases, or from PCR products amplified from target genes coding regions, where the primers used for the PCR reactions are modified by the addition of phage T3 and T7 promoters. The resulting sense and antisense RNAs are annealed in an injection buffer and the double-stranded RNA injected into *C. elegans* hermaphrodites. Progeny of the injected hermaphrodites are inspected for phenotypes-of-interest. Other methods can also been employed for generating mutant phenotypes in nematodes using single-stranded antisense DNA or RNA species, as described above. However, single-stranded methods may be less effective in nematodes than that of double-stranded RNA interference (see Guo and Kemphues, 1995, Cell 81:611–620; see also Fire, 1991, Development 113:503–514).

5.4.4. Transgene Mediated Overexpression of Target Genes

The present invention provides target strains of *C. elegans* which overexpress a target gene for use in a TDS screen. Promoters which may be used to control target gene overexpression include, but are not limited to, the SV40 early promoter region (Benoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), the regulatory sequence of the human cytomegalovirus for expression in any tissues (Foecking, M. and Hofstetter, H., 1986, Gene 45:101–105; U.S. Pat. No. 5,168,062). Temperature-induced expression of a target gene can be controlled by heat shock gene promoters hsp 16–2 and hsp 16–41.

In a specific embodiment, a gene fusion comprising a constitutive or heat shock-induced promoter functionally linked to a target and/or reporter gene is incorporated into a transformation vector. The transformation vector also comprises a dominant selectable marker, such as rol-6. The procedure for microinjection is preferably carried out according to the methods of Fire et al. (1986, EMBO J. 5:2673–2680). Transgenic animals for use as target strains are identified as those exhibiting a roller phenotype. The decoy strain is generated by transforming worms with a vector comprising the dominant selectable marker but not the target or reporter gene.

5.5. Bacterial Methodology

The invention provides bacterial cells that have been modified to overexpress a protein whose inhibition reduces cell fitness or viability, or in an alternative embodiment, increases cell fitness or viability. Such bacterial cells are used in accordance with the TDS methods described in the present application.

The nucleotide sequence encoding the protein for which an inhibitor is sought, or a functionally active analog or fragment or other derivative thereof, can be inserted into an appropriate expression vehicle, e.g., a plasmid which contains the necessary elements for the transcription and translation of the inserted protein-coding sequence. The necessary transcriptional and translational signals can be supplied from the native gene and/or its flanking regions. Alternatively, an expression vehicle is constructed by inserting a structural DNA sequence encoding a desired protein together with suitable translation initiation and termination signals in operable reading phase with a functional promoter using one of a variety of methods known in the art for the manipulation of DNA. See, generally, Sambrook et al., 1989, *Molecular Biology: A Laboratory Manual*, Cold Spring Harbor Press, Cold Spring Harbor, N.Y.; Ausubel et al., 1995, *Current Protocols in Molecular Biology*, Greene Publishing, New York, N.Y. These methods may include in vitro recombinant DNA and synthetic techniques and in vivo recombinants (genetic recombination).

In certain specific embodiments of the invention, the expression vehicle of the target protein is a plasmid. Large numbers of suitable plasmids are known to those of skill in the art and are commercially available for generating the recombinant constructs of the present invention.

Such commercial plasmids include, for example, pKK223-3 (Pharmacia Fine Chemicals, Uppsala, Sweden) and GEM 1 (Promega Biotec, Madison, Wis., USA). These pBR322 "backbone" sections are combined with an appropriate promoter and the structural sequence to be expressed. pBR322 is considered to be a low copy number plasmid. If higher levels of expression are desired, the plasmid can be a high copy number plasmid, for example a plasmid with a pUC backbone. pUC plasmids include but are not limited to pUC19 (Yanish-Perron et al., 1985, Gene 33:103) and pBluescript (Stratagene).

Other expression plasmids which may be used in conjunction with the methods of the invention include but are not limited to: pBs, phagescript, PhiX174, pBluescript SK, pBs KS, pNH8a, pNH16a, pNH18a, pNH46a (Stratagene); pTrc99A, pKK223-3, pKK233-3, pDR540, pRIT5 (Pharmacia); and GEM 1 (Promega Biotec, Madison, Wis., USA).

The present invention also provides bacteria that overexpress a target protein via transposon-mediated chromosomal integration of the protein's coding sequence. Any transposon plasmid known in the art may be used in the methods of the invention so long as a nucleic acid encoding the target protein can be constructed into the transposon cassette. For example, the invention provides a transposon plasmid, comprising a transposon or minitransposon, and a MCS.

In certain embodiments of the invention, the plasmid of the invention is a transposon plasmid, i.e., comprises a transposon in which the sequence encoding the target protein is inserted. Transposon plasmids contain transposon cassettes which cassette becomes integrated into the bacterial genome. Accordingly, a nucleic acid encoding a target protein or an active fragment or analog thereof is inserted into the transposon cassette. Thus, a transposon insertion integrates the cassette into the bacterial genome. The coding sequence can be operably linked to a promoter, or can be promoterless. In the latter case, expression of the target protein is driven by a promoter at the site of transposon insertion into the bacterial genome. Colonies of bacteria having a transposon insertion are screened for expression levels that meet the requirements of the invention.

In certain embodiments, in addition to the transposon, the transposon plasmid comprises outside the inverted repeats of the transposon a transposase gene to catalyze the insertion of the transposon into the bacterial genome without being carried along with the transposon, so that bacterial strains with stable transposon insertions are generated.

Transposons to be utilized by the present invention include but are not limited to Tn7, Tn9, Tn10 and Tn5. In a preferred embodiment, the transposon plasmid is pBR322 (ATCC) having an ampicillin resistance gene located outside the Tn10 insertion elements and the nucleic acids encoding a target protein and optionally a reporter protein is inserted between the two Tn10 insertion elements (e.g., within the transposon cassette).

In one embodiment, after the manipulation of the plasmid as appropriate and selection of those clones having the desired construct using the ampicillin resistance properties encoded by the plasmid, the antibiotic selection is removed and strains having a chromosomal transposon insert are chosen for screening according to the methods of the present invention.

In a preferred embodiment, a transposon plasmid for selection of transposon-mediated chromosomal integrants, comprises a transposase gene, for transposon excision and integration; a coding sequence corresponding to a selection gene that has been deleted from the bacterial strain as well as a ribosomal binding site and terminator for the wild-type gene, but lacking a promoter; and a multiple cloning site (MCS) containing unique restriction sites within the plasmid, for the incorporation of a nucleic acid encoding the target protein and optionally a reporter gene.

In yet another embodiment, the expression vehicle is an extrachromosomal plasmid that is stable without requiring antibiotic selection, i.e., is self-maintained. For example, in one embodiment of the invention, the plasmid selection system is maintained by providing a function which the bacteria lacks and on the basis of which those bacteria having the function can be selected for at the expense of those that do not. In one embodiment, the bacteria of the invention is an auxotrophic mutant strain and the expression plasmid provides the mutant or absent biosynthetic enzyme function. The bacteria which contain the expression plasmid can be selected for by growing the cells on growth medium which lacks the nutrient that only the desired cells, i.e., those with the expression plasmid, can metabolize.

In other embodiments of the invention, the expression vehicle is a λ vector, more specifically a lysogenic λ vector.

In a certain specific embodiment, the bacterial host comprising the λ vector further comprises a temperature-sensitive λ repressor which is functional at 30° C. but not 37° C. Consequently, the bacterial host can be grown and manipulated at 30° C. without expression of the target protein. When the TDS screen is carried out, the cells are grown at 37° C., at which temperature the λ repressor is inactivated and the expression of the target protein, and optionally a the reporter gene, is activated.

Expression of a nucleic acid sequence encoding a target protein may be regulated by a second nucleic acid sequence so that the protein is expressed in a bacteria transformed with the recombinant DNA molecule. Expression of target protein may be controlled by any promoter/enhancer element known in the art. A promoter/enhancer may be homologous (e.g., native) or heterologous (e.g., not native). Promoters which may be used to control the expression of the target protein and optionally the reporter gene in bacteria include, but are not limited to prokaryotic promoters such as the β-lactamase promoter (Villa-Kamaroff et al., 1978, Proc. Natl. Acad. Sci. U.S.A. 75:3727–3731), or the lac promoter (DeBoer et al., 1983, Proc. Natl. Acad. Sci. U.S.A. 80:21–25; Scientific American, 1980, 242:74–94). Other promoters encompassed by the present invention include but are not limited to lacI, lacZ, T3, T7, gpt, lambda $P_R$, lambda $P_L$, and trc.

Once a plasmid is constructed comprising the coding sequence for the target protein is introduced into the bacteria to produce a target cell, target protein expression can be assayed by any method known in the art including but not limited to biological activity, enzyme activity, Northern blot analysis, and Western blot analysis. (See Sambrook et al., 1989, *Molecular Biology: A Laboratory Manual*, Cold Spring Harbor Press, Cold Spring Harbor, N.Y.; Ausubel et al., 1995, *Current Protocols in Molecular Biology*, Greene Publishing, New York, N.Y.).

In order for the methods of the invention to succeed, it is imperative that the reporter gene and the nucleic acid encoding the target protein be tightly linked. This may be achieved by any one of several means, including expression of both coding sequences from one plasmid or having both coding sequences integrated into the bacterial genome. In all embodiments, expression of the reporter gene is constitutive under screening conditions.

When the target cell of the invention is a modified bacterial cell that either (a) expresses the target protein from a plasmid or extragenomic transposon, or (b) has an additional copy of the target protein coding sequence integrated into the bacterial chromosome, the decoy cell is then (a) an isogenic or otherwise not substantially different bacterial cell that carries an "empty" plasmid, when the expression vehicle for the target protein is a plasmid or extragenomic transposon; or (b) an isogenic or otherwise not substantially different bacterial cell whose genome lacks the additional copy of coding sequence for the target protein and lacks substantial expression of the reporter gene, when the nucleic acid encoding the target protein has been integrated into the chromosome.

5.6. Plant Methodology

The TDS screens of the invention can also be employed using plant cells. The invention provides target plant cells that have been modified to overexpress a protein whose inhibition reduces or alternatively increases, cell fitness or viability. The invention further provides decoy plant cells that have been modified to underexpress a protein whose inhibition reduces or increases cell fitness or viability. A variety of plant expression systems may be utilized to carry out the TDS methods of the present invention. Particular plant species may be selected from any dicotyledonous, monocotyledonous species, gymnospermous, lower vascular or non-vascular plant, including any cereal crop or other agriculturally important crop. Such plants include, but are not limited to, alfalfa, Arabidopsis, asparagus, barley, cabbage, carrot, celery, corn, cotton, cucumber, flax, lettuce, oil seed rape, pear, peas, petunia, poplar, potato, rice, soybean, sugar beet, sunflower, tobacco, tomato, wheat and white clover.

Overexpression of a target gene in plant cells by recombinant means can be achieved by one of the following methods, which are well-known to those skilled in the art (see, for example, Plant Biotechnology, 1989, Kung & Arntzen, eds., Butterworth Publishers, ch. 1, 2, which chapters are incorporated herein in their entireties). Examples of transformation methods which may be effectively used to generate a target cell include but are not limited to Agrobacterium-mediated transformation of leaf discs or other plant tissues, microinjection of DNA directly into plant cells, electroporation of DNA into plant cell protoplasts, liposome or spheroplast fusion, microprojectile bombardment, and the transfection of plant cells or tissues with appropriately engineered plant viruses.

Plant tissue culture procedures that can be used to practice the invention are well-known to those skilled in the art (see for example, Dixon, 1985, Plant Cell Culture: A Practical Approach, IRL Press). Those tissue culture procedures that may be used effectively to practice the invention include the production and culture of plant protoplasts and cell suspensions, sterile culture propagation of leaf discs or other plant tissues on media containing engineered strains of transforming agents such as, for example, Agrobacterium or plant virus strains and the regeneration of whole transformed plants from protoplasts, cell suspensions and callus tissues.

Plant transformation methods are additionally described by Davey et al., Plant Mol. Biol. 13:273–285, and in chapter nine of Grierson & Covey (1988, Plant Molecular Biology, $2^{nd}$ Edition, Blackie and Sons Ltd, Glasgow, Scotland; published in the United States by Chapman & Hall, New York). General and specialized plant culture methods, including methods to isolate mutants from cell culture, can also be found in Handbook of Plant Cell Culture, Volume 1, 1983, Macmillan Publishing Company, New York, Evans, Sharp, Ammirato, and Yamada, Eds., chapters 1–6, 10, 14 and 15. Further considerations for successful large-scale plant cell cultures are described by Taticek et al., 1994, Curr. Opin. Biotechnol. 5:165–174; and Scragg, 1992, Curr. Opin. Biotechnol. 3:105–109.

Wullems et al. (1986, Handbook of Plant Cell Culture, Volume 4, Macmillan Publishing Company, New York, Evans, Sharp and Ammirato, Eds.) provide a detailed protocol on plant transformation via Agrobacterium Ti plasmid. Transformation via electroporation is described by Bates, 1999, Methods Mol. Biol. 111:359–366. For monocotyledonous plants, which are particularly resistant to the uptake of foreign DNA, geminiviruses can be used for recombinant gene expression (see Stanley, 1993, Curr. Opin. Genet. Devel. 3:91–96).

Methods to identify plant mutants other than those provided in the Handbook of Plant Cell Culture, supra, are described by Walden et al, 1994, Plant Mol. Biol. 26:1521–1528 and by Langridge, 1994, Bioessays 16:775–778.

Methods to construct the expression constructs and transformation vectors include standard in vitro genetic recombination and manipulation. See, for example, the techniques described in Weissbach and Weissbach, 1988, Methods For Plant Molecular Biology, Academic Press, Chapters 26–28.

Regulatory elements that may be used in plant cell expression constructs comprising a target and/or reporter gene include promoters which may be either heterologous or homologous to the plant cell. The promoter may be a plant promoter or a non-plant promoter which is capable of driving high levels transcription of a linked sequence in plant cells and plants. Non-limiting examples of plant promoters that may be used effectively in practicing the invention include cauliflower mosaic virus (CaMV) 35S, rbcS, the promoter for the chlorophyll a/b binding protein, Adhli, NOS and HMG2.

5.7. Reporter Genes

The reporter gene used to mark the target cell of the invention can be selected from any reporter gene known in the art. In one embodiment, the reporter gene can be a gene encoding a fluorescent protein, a bioluminescent protein, a chemiluminescent protein, an enzyme (e.g., bacterial lacZ protein or chloramphenicolacetyl transferase (CAT)), a receptor, a transporter protein or ion channel (such as the cystic fibrosis transporter protein), or a protein comprising an immunologically detectable epitope or other binding moiety (e.g., CD4 cell surface antigen, myc, glutathione-S-transferase (GST), or hexahistidine).

In a specific embodiment, the reporter gene encodes a transporter protein or reporter channel. Reporter gene activity is a function of the transport of ions and/or molecules across the cell membrane. When reporter gene activity results in increased ionic flow, the activity can be measured electrophysiologically (for e.g. $Na^+$, $K^+$ or $Cl^-$ ions) or by a dye that binds to the ion (for e.g. $Ca^{++}$ ions).

In a preferred embodiment, lacZ is used as a reporter gene. β-galactosidase activity can be measured by one of several means. If the co-culture cells are yeast or bacterial cells, filter β-galactosidase assays can be performed as modified from the protocol of Breeden and coworkers (Breeden and Nasmyth, 1985, Cold Spring Harb. Symp. Quant. Biol. 50:643–650). Yeast or bacterial co-cultures are dot blotted on Whatman paper and dots that are positive for β-galactosidase activity turn blue. Alternatively, the yeast or bacteria can be grown in indicator media comprising β-galactosidase substrate X-gal. Quantitative β-galactosidase assays on yeast can be performed as described previously by Coney and Roeder (Coney and Roeder, 1988, Mol. Cell. Biol. 8:4009–4017). Chemiluminescent β-galactosidase assays can be performed by using the Galacto-Light and Galacto-Light Plus Chemiluminescent reporter assay system for the detection of β-galactosidase (Tropix, Inc.) according to the manufacturer's protocols. Fluorescent β-galactosidase assays can be performed using the FluoReporter lacZ/Galactosidase Quantitation kit (Molecular Probes) according to the manufacturer's protocols. For co-culture assays using cultured cells or C. elegans, β-galactosidase activity can be detected by determining enzymatic activity in situ by adding substrate to the media, as modified from the protocol of Breeden and coworkers (Breeden and Nasmyth, 1985, Cold Spring Harb. Symp. Quant. Biol. 50:643–650).

In a most preferred embodiment, the reporter gene encodes a fluorescent molecule, e.g., firefly luciferase. In a preferred mode of the embodiment, the protein encoded by the reporter gene is GFP from Aequorea victoria or a mutant thereof. The GFP can be encoded by its naturally occurring coding sequence or by a coding sequence that has been modified for optimal human codon usage (U.S. Pat. No. 5,874,304) when screening in a mammalian cell line. Mutations can be introduced into the coding sequence to produce GFP mutants with altered fluorescence wavelength or intensity or both. Such mutations are largely in the vicinity of residues 65–67, which form the chromophore of the protein. Examples of useful GFP mutations for use as reporter genes according to the methods of the present invention can be found in U.S. Pat. Nos. 5,777,079 and 5,804,387 and International Publication WO97/11094. In another preferred mode of the embodiment, the GFP mutant is a blue GFP. Examples of blue GFPs are described by Heim and Tsien (1996, Curr. Biol. 6:178–82). In yet another preferred mode of the embodiment, the fluorescent protein is a yellow or red-orange emitter recently discovered in reef corals (Matz et al., 1999, Nature Biotechnol. 17:969–973).

In one embodiment, the reporter of the invention can be expressed as a fusion protein with the target protein.

The promoter elected for controlling reporter gene expression depends on the type of cell or organism in which the reporter is expressed. Suitable promoters for each organism are described in Sections 5.2.2., 5.3.4, and 5.4.4., supra.

5.8. Use of Target Genes That Negatively Contribute to Cell Fitness

As described above, in one embodiment of the invention, the target protein positively contributes to the fitness of the target cell. However, in an alternative embodiment, described in this section, the target protein negatively contributes to the fitness of the target cell (e.g., provides overexpression lethality). Cells of various genetic backgrounds (e.g., deletion libraries) can be surveyed in order to identify the cell strain in which overexpression of the desired target gene negatively contributes to the fitness of the cell, or the optimal (most sensitive) cell strain for the same.

In such an embodiment, the invention provides a method for screening for a molecule that inhibits the activity or expression of a protein encoded by a target gene, comprising co-culturing a first cell or group of first cells and a second cell or group of second cells in the presence of a test molecule, wherein the first cell has higher expression or activity of a target gene or a protein encoded by the target gene relative to the second cell, wherein said protein encoded by the target gene negatively contributes to the fitness of the first cell, wherein the first cell further comprises and expresses a reporter gene that is substantially not expressed in said second cell, wherein the first cell and second cell are of the same species and cell type, and wherein the ratio of the number of first cells to second cells in the co-culture initially is greater than one; and measuring the activity or amount of protein encoded by the reporter gene, wherein the lack of a decrease in activity or amount of protein encoded by the reporter gene relative to that in the co-culture in the absence of the test molecule indicates that the test molecule inhibits the activity or expression of the protein encoded by the target gene. Such a co-culture screen can identify inhibitors against pre-selected genes, preferably human genes. The screen identifies inhibitors that rescue fitness defects caused by overexpression of a target gene. If overexpression of a target gene causes a growth defect in the target cell, then an inhibitor that targets the target protein should rescue the growth defect. A company called Iconix Pharmaceuticals, Inc. currently screens for inhibitors of human targets based on rescue of growth defects caused by overexpression of a target gene. See, httn:// www.iconixpharm.com/scitech.library.html.

The present invention improves technology used by Iconix Pharmaceuticals, Inc. in two significant ways:

1) Competitive growth experiments with large collections of bar-coded deletion strains could be used to identify genetic background(s) with increased sensitivity to the overexpression lethal phenotype of various human genes.
2) The co-culture assay proves a much more sensitive and robust way to identify subtle differences in growth rates caused by inhibitors that rescue the overexpression lethal phenotype in yeast.

This embodiment is illustrated by way of example in Section 11, infra.

The embodiment of the invention wherein the target gene negatively contributes to the fitness of the cell that relatively overexpresses the target gene can also be multiplexed, by methods such as described herein for the embodiment wherein the target gene positively contributes to the fitness of the cell (see, e.g., Section 5.9.1, "Multiplex Screens").

5.9. Variations on the TDS Methods

The present invention provides variations on the TDS methods described herein. In one embodiment, the variations provide large scale targeted screening by "multiplexing", i.e. concurrent screening for inhibitors of multiple target genes. In another embodiment, the variations provide differential targeted screening for inhibitors of one target gene but not a functionally similar target gene.

5.9.1. Multiplex Screens

In certain preferred embodiments of the present invention, the TDS screen is multiplexed for more efficient and cost-effective screening. Multiplexing entails the use of more than one target strain, each of which overexpresses a different target gene. The corresponding decoy cell is a wild type cell. In a multiplex screen, care should be taken to ensure that the combined reporter gene activity from all target cells does not generate a high noise:signal ratio.

The target cells can express the same reporter gene or different reporter genes. If the cells express the same reporter gene, a secondary round of screening is used to identify in a co-culture having significantly increased levels of reporter gene activity which of the target cells is the source of said increased reporter gene activity, i.e. to determine which is the target gene of the drug with which treatment of a co-culture resulted in increased reporter gene activity. Secondary screening can be carried out using a variety of methods. In one non-limiting example, non-multiplex TDS screens are used for secondary screening, wherein each co-culture comprises the decoy strain and only one or a subset of the target cells. Alternatively, secondary screening can be carried out using the polymerase chain reaction (PCR), more preferably quantitative PCR, in which pairs of oligonucleotide primers are used that are specific for each recombinant target cell. In a preferred mode of the embodiment, an aliquot of the co-culture is used as the template in a set of PCR reactions, with each reaction containing a pair of primers specific to a plasmid harboring one of the target genes and a target gene harbored by that plasmid. Preferably, the primers are designed so that each PCR reaction that tests for the presence of a target gene of the multiplex screen produces a distinct amplicon size, so that the presence or absence of a PCR product of a given size, or the ratio of PCR products obtained, is indicative of which target gene is amplified. In yet another non-limiting example, secondary screening can be carried out by growing the co-culture, consisting primarily of those target cells having increased reporter gene activity, on selective growth media if the different target cells have different auxotrophic requirements. For example, each of the e.g., yeast target cells is deficient for a different nutrient (biosynthesis) pathway, and the secondary screen entails plating an aliquot of the co-culture on a variety of media, each of which lacks a nutrient necessary for the growth of one of the target cells. The identification of the target cell that is the source of the increased reporter activity can then be made based on which of the media plates have few or no yeast colonies.

Target cells in a multiplex assay which express different target genes optionally can each express a different reporter gene. Alternatively, the target cells are divided into pools, each pool expressing a different reporter gene to simplify secondary screening processes. In yet another embodiment, the target cells express non-identical combinations of reporter genes to generate a reporter gene code for instant identification of the target cell with increased reporter gene activity. In a preferred mode of the embodiment, each target cell expresses a unique combination of one or more of GFP, blue GFP, yellow fluorescent protein and red fluorescent protein.

5.9.2. Species- and Isoform-specific Screens

In certain preferred embodiments of the present invention, the TDS screen is used to identify a molecule that inhibits a target protein expressed by a target cell but not a functionally similar protein expressed in the corresponding decoy cell. In such an embodiment, the target protein positively contributes to the fitness of the target cell.

As used herein, a gene or protein that is "functionally similar" to a target gene indicates a gene or protein with the capability of rescuing all or a partial loss of function of the target gene or protein, respectively.

In a specific embodiment, a TDS screen to identify a molecule that differentially inhibits a target protein but not another functionally similar protein comprises co-culturing a target cell and decoy cell wherein the target cell has elevated expression or activity relative to the decoy cell of (a) a target gene that positively contributes to cell fitness, or (b) the protein encoded by the target gene, and the decoy cell has elevated expression or activity of a functionally similar gene or the protein encoded by said functionally similar gene relative to the target cell. As with the basic TDS screen, this modified screen then entails exposing the co-culture to a test molecule or a panel of test molecules, then detecting whether treatment with the test molecule produces a significant increase in the activity or amount of protein encoded by the reporter gene expressed by the target cell; if so, the test molecule is indicated to be an inhibitor of the target protein but not the functionally similar protein.

In one embodiment, a functionally similar gene can be a partially or fully redundant gene of the same species as the target gene. In another embodiment, a functionally similar gene can encode a protein with similar activities as the target protein, such as isozyme which may be expressed in the same or a different cell or tissue type than the target protein.

Such a variant of the TDS screen may be carried out when it is desired to inhibit a target gene causing an ailment but not a related gene, for example, an isozyme expressed in a different tissue, whose inhibition results in undesired side effects. An example of such a screen would entail expression of COX2 in a target cell and COX1 in a decoy cell. COX1 is a ubiquitously expressed cyclooxygenase whose inhibition in the gut as a result of administration of non-steroidal anti-inflammatory drugs (NSAIDS), produces nausea, while the anti-inflammatory analgesic properties of NSAIDS are mediated by the inhibition of COX2 activity. (See, e.g., Masferrer et al., 1996, Gastroenterol. Clin. North Am. 25:363–372.). Thus, identifying an inhibitor specific to COX2 according to the methods of the present invention can allow the development of analgesics that target COX2 but do not produce the side effects of inhibiting COX1.

In another embodiment, a functionally similar gene can be a homolog of the target gene from another species. This embodiment can be used to screen for inhibitory molecules that are species specific. For example, if the purpose of the screen is to identify an anti-fungal agent for the treatment of mammals such as humans, a target gene which has a mammalian homolog can be used to generate a target cell, as long as a decoy cell expresses the mammalian homolog of the gene at comparable or higher levels than the levels of the target gene expression in the target cell. If the purpose of the screen is to identify an insecticide that is safe for humans, the target gene can be an insect gene with a human homolog, as long as the target cell over expresses the insect gene and the decoy cell over expresses the human homolog at comparable or higher levels.

In yet another embodiment, a functionally similar gene can encode a protein encoded by an alternative spliced DNA encoded by the target gene or a gene from which the target gene is derived, e.g., if the target gene is derived from a cDNA the gene from which it is derived would the corresponding genomic sequence. In yet another embodiment, a functionally similar gene can encode a mutant target protein having amino acid substitutions, for example, in those amino acids which are desired to be targeted, or a mutant target protein having a deletion in a particular domain which is desired to be targeted by the TDS screen.

5.10. Microbial Organisms for TDS Screening

The antibiotic compounds identified by the methods of the invention, i.e. those that inhibit a gene in a microorganism that positively contributes to the fitness of the microorganism, can be used to treat infectious diseases caused by such bacteria in animals, including humans, companion animals (e.g., dogs and cats), livestock animals (e.g., sheep, cattle, goats, pigs, and horses), laboratory animals (e.g., mice, rats, and rabbits), and captive or wild animals.

In certain embodiments, the TDS screens of the invention are directed to drug discovery for treatment of diseases caused by bacteria and other microorganisms by identifying molecules that inhibit a target gene of the bacteria or microorganism that cause the diseases. Such microorganisms include but are not limited to, gram positive cocci, such as Staphylococci (e.g., *S. aureus*), Streptococci (e.g., *S. pneumoniae, S. pyrogens, S. faecalis, S. viridans*); gram positive bacilli, such as Bacillus (e.g., *B. anthracis*), Corynebacterium (e.g., *C. diphtheriae*), Listeria (e.g., *L. monocytogenes*); gram negative cocci, such as Neisseria (e.g., *N. gonorrhoeae, N. Meningitidis*); gram negative bacilli, such as Haemophilus (e.g., *H. influenzae*), Pasteurella (e.g., *P. multocida*), Proteus (e.g., *P. mirabilis*), Salmonella (e.g., *S. typhi murium*), Shigella species, Escherichia (e.g., *E. coli*), Klebsiella (e.g., *K. pneumoniae*), Serratia (e.g., *S. marcescens*), Yersinia (e.g., *Y. pestis*), Providencia species, Enterobacter species, Bacteroides (e.g., fragilis), Acinetobacter species, Campylobacter (e.g., *C. jejuni*), Pseudomonas (e.g., *P. aeruginosa*), Bordetella (e.g., *B. pertussis*), Brucella species, Fracisella (e.g., *F. tularensis*), Clostridia (e.g., *C. perfriugens*), Helicobacter (e.g., *H. pylori*), Vibrio (e.g., *V. cholerae*), Mycoplasma (e.g., *M. pneumoniae*), Legionella (e.g., *L. pneumophila*), Spirochetes (e.g., Treponema, Leptospira and Borrelia), Mycobacteria (e.g., *M. tuberculosis*), Nocardia (e.g., *N. asteroides*), Chlamydia (e.g., *C. trachomatis*), and Rickettsia species.

5.11. Kits and Assay Systems

The invention also provides kits for carrying out the screening methods of the invention. Such kits comprise in one or more containers a purified population a target cell and a purified population of a decoy cell of the same species and cell type, wherein the target cell has elevated expression or activity of the target gene or the protein encoded by the target gene relative to the decoy cell and further comprises and expresses a reporter gene encoding a bioluminescent, chemiluminescent or fluorescent molecule that is substantially not expressed in the decoy cell.

In one embodiment, a target cell and decoy cells are bacterial cells, yeast cells, cultured insect cells, cultured mammalian cells or cultured plant cells. In another embodiment, the fluorescent molecule is GFP or a mutant thereof having an altered fluorescence wavelength, increased fluorescent, or both.

In another embodiment, the kit further comprises in addition to a first target cell and the decoy at least one second target cell having elevated expression or activity of a second target gene or the protein encoded by the second target gene relative to the decoy cell and first target cell, and further comprises and expresses a reporter gene encoding a bioluminescent, chemiluminescent or fluorescent molecule that is substantially not expressed in the decoy cell or the first target cell.

In another embodiment, the kit further comprises a molecule known to inhibit the target gene or the protein encoded by the target gene to serve as a control molecule during the screening process.

Instructions are optionally included for using the cells provided to carry out the screening methods of the present invention.

Assay systems of the invention are also provided, which comprise the co-cultures used in the TDS screens.

5.12. Pharmaceutical Applications

Molecules identified by the methods of the present invention as having inhibitory activity against a specific target gene are candidate lead compounds for drug development. A lead compound can be assayed for its effectiveness towards the specific condition at which it is directed, its side effects, etc. A lead compound can be chemically modified, e.g. derivatized, to improve activity and specificity.

In certain embodiments of the present invention, the lead compound targets a disorder of increased cellular proliferation, including but not limited to neoplastic changes, malignancy, dysproliferative changes (such as metaplasias and dysplasias), or other hyperproliferative disorders. The treatment can be preventative or therapeutic.

Similarly, potential anti-fugal compounds can be tested in heterologous host cell systems (e.g., human cells) to verify they do not affect proliferation or other cell functions to a significant degree. For instance, potential anti-fungal compounds can be used in a mammalian Genome Reporter Matrix system to make sure that the compounds do not adversely alter gene transcription (e.g., in an undesirable way). Similarly, potential anti-proliferative compounds can be tested to be sure that they do not adversely affect functions other than proliferation. Potential herbicidal and insecticidal compounds can also be tested for potential side effects in mammalian, preferably human, cell systems, such as the Genome Reporter Matrix system, for potential side effects on cellular functions. Of course, certain changes in gene transcription may be inevitable and many of these will not be deleterious to the patient or host organism. As mentioned above, once lead compounds have been identified, these compounds can be refined further via rational drug design and other standard pharmaceutical techniques. Ultimately, compounds can be used as effective antibiotics, anti-fungal agents, anti-proliferative drugs, herbicides and pesticides.

The compounds of this invention having human and animal applications (i.e., human or veterinary therapeutics) can be formulated into pharmaceutical compositions and administered in vivo at an effective dose to treat a particular disease or disorder. Determination of a preferred pharmaceutical formulation and a therapeutically efficient dose regiment for a given application is within the skill of the art taking into consideration, for example, the condition and weight of the patient, the extent of desired treatment and the tolerance of the patient for the treatment. Administration of the compounds of this invention, (including isolated and purified forms, their salts or pharmaceutically acceptable derivatives thereof), to a human or animal may be accomplished using any conventionally accepted mode of administration.

The pharmaceutical compositions comprising molecules identified by the methods of the present invention may be administered to a subject such as a plant, human or animal in order to treat bacterial or fungal diseases or proliferative disorders. Such animals to be treated by the pharmaceutical compositions of the present invention include non-human mammals including but not limited to monkeys and other primates, dogs, cats, ferrets, guinea pigs, cattle, sheep, pigs, goats and horses, and birds.

Anti-fungal agents identified by the methods of the present invention may further be used to prevent contamination of mammalian and non-mammalian cells (e.g., insect cells) grown in tissue culture by fungi, e.g., yeast, by incubating such cells in cell culture medium containing an effective amount of the agent.

Alternative embodiments for implementing the screening methods of this invention will be apparent to one of skill in the art and are intended to be comprehended within the accompanying claims. In particular, the accompanying claims are intended to include alternative types of cells or organisms as screening models, reporter genes, methods for overexpressing and underexpressing target and reporter genes, classes of molecule to be identified by the targeted screens, variations on the screening methods, etc.

The following experimental examples are offered by way of illustration and not by way of limitation.

6. IDENTIFICATION OF INHIBITORS FOR A TARGET THAT IS ESSENTIAL FOR NORMAL GROWTH IN *SACCHAROMYCES CEREVISIAE*

This example describes a series of experiments that show the feasibility of co-cultures for drug screening in yeast using the TDS method and erg11 as a target gene.

6.1. Determining of the Signal to Noise Ratio of the TDS Assay in Yeast

The decoy cell was ABY11 (MATa, ura3–1Δleu2–1Δ). The target cell was ABY11 that harbored a plasmid expressing GFP from the yeast DDR2 promoter (pDW415). Freshly grown yeast cells were resuspended in YM medium plus 2% casamino acids (YM-Cas). Culture density was determined by reading the absorbance of the cultures at 600 nm in a Shimadzu BioSpec 1601 spectrophotometer. Cell densities were calculated using the following conversion factor: 1 O.D.600 unit=$1.5 \times 10^7$ cells per ml.

Cells were dispensed to wells of a 96-well plate at a constant total number of $5 \times 10^7$ cells per ml in a total volume of 225 μl in YM medium plus 2% casamino acids. The composition of the cell mixtures varied from 100% target cells to 100% decoy cells. The amount of fluorescence emitted from the cultures was quantitated in a Molecular Dynamics Vistra FluorImager. Plate imaging took place immediately after preparing the mixtures to avoid cell growth.

The amount of fluorescence emitted from the cell mixtures was not linear with respect to the dilution factor (FIG. 1). At dilutions of decoy: target of greater than about 10, the detectable fluorescent output of the cell mixtures was close to background. When the target cells were present at greater than 10% of the cell population, the fluorescent output of the mixtures increased significantly. This result suggested that a decoy: target ratio of greater than, or equal to, 10 would yield a successful co-culture assay. In other words, if a drug candidate were tested that led to the target cell's relative abundance in the population to increase to more than 10%, then a large fluorescent signal would result.

6.2. Determining of the Sensitivity of the TDS Assay in Yeast

The sensitivity of the TDS assay is determined by the difference in growth rates between the target and decoy cells and the number of population doublings that the mixture can go through before reaching saturation (~$3 \times 10^7$ cells/ml for yeast). The number of population doublings is determined by the culture volume and the number of starting cells. For example, a 200 μl culture inoculated with 1025 cells (1000 decoy and 25 target) will reach saturation after ~13 population doublings. Table 2 illustrates how the difference in the growth rates between the target and decoy cells affect the results of the TDS assay. The calculations are based on a 200 μl culture that was inoculated with 1025 cells which were allowed to grow to saturation ($3 \times 10^7$ cells/ml). These numbers suggest that a 50% difference in growth rate between the target and decoy cell is required to generate a detectable signal in the TDS assay. The sensitivity of the assay can be improved by increasing the number of population doublings. This can be accomplished by increasing the culture volume or by diluting the cultures by adding fresh drug containing media.

| Percent Growth Difference | Doubling Time | | Starting ratio Target:decoy | Final ratio Target:decoy | Predicted Signal to noise |
|---|---|---|---|---|---|
| | Target | Decoy | | | |
| 0% | 100 min | 100 min | 0.001 | 0.001 | 0 |
| 20% | 100 min | 120 min | 0.001 | 0.007 | 0 |
| 50% | 100 min | 150 min | 0.001 | 0.12 | 10 |

-continued

| Percent Growth Difference | Doubling Time | | Starting ratio | Final ratio | Predicted Signal to noise |
| --- | --- | --- | --- | --- | --- |
| | Target | Decoy | Target:decoy | Target:decoy | |
| 75% | 100 min | 175 min | 0.001 | 0.91 | 40 |
| 100% | 100 min | 200 min | 0.001 | 3.6 | 60 |
| 1000% | 100 min | 1000 min | 0.001 | 3194 | 80 |

Table 2. Sensitivity of the TDS assay. The calculations are based on a theoretical experiment where different 200 µl cultures were inoculated with 1025 cells (1000 decoy and 25 target) which were allowed to grow to saturation ($3 \times 10^7$ cells/ml). The doubling times of the target cell was held constant at 100 minutes while the doubling time of the decoy cell was varied from 100 to 1000 minutes. The "starting" and "final" target:decoy ratios are listed for each of the different co-culture experiments. The predicted "Signal to Noise" was based on the data from the mixing experiment in FIG. 1. This demonstrates that a 50% or more difference in growth rates generates a detectable fluorescent signal.

6.3. Pilot Study with Clotrimazole

To determine the optimal assay conditions, various target:decoy ratios were tested in the presence of different clotrimazole concentrations (FIG. 2). Clotrimazole is an anti-fungal compound that inhibits the ERG1 gene product, lanosterol 14α-demethylase, a sterol biosynthetic enzyme (Georgopapadakou and Walsh, 1996, Antimicrob Agents Chemother 40:279–291). The target cell ABY676 harbors two plasmids, pAB98 and pAB99, which express GFP and ERG11 at high levels, respectively. The decoy cell ABY674 harbors two control vectors, YEplac 195 and YEplac 112.

Target and decoy cells were mixed at 1:10, 1:100 and 1:1000 ratios in the presence of various concentrations of clotrimazole. In addition, the total number of cells was varied by serial dilution and is indicated at the top panel of FIG. 2A. Cells were mixed in a volume of 225 µl of YM-Cas medium in each well. Following incubation at 30° C. for 88 h, the fluorescence from each well was determined. The fluorescent values were corrected for the background fluorescence of the medium are represented as the fold increase over the fluorescent signal from the corresponding no-drug treatment.

Figures 2A, 2B, 2C:
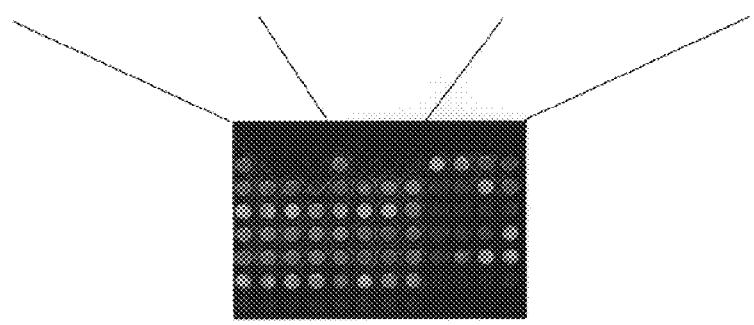

The amount of growth of the cells was determined by measuring optical density at 600 nm in a Molecular Devices Spectra Max 250 plate spectrophotometer (FIG. 2B). A fluorescent image of the plate, which served as the source for quantitation of the fluorescent signals, is also presented (FIG. 2C).

This experiment revealed that the co-cultures produced a large signal to noise ratio over a large concentration range of clotrimazole. The fluorescent signals were also significantly greater than the no-drug treatment in all three decoy: target ratios and at all variations in total cell number/well. More specifically, the 1:10 and 1:100 target: decoy ratios produced significant signals from 0.2–5.6 µg/ml at the highest density of cells per well. The serial dilutions of cells at these ratios produced significant fluorescent signals at 0.2–2.8 µg/ml clotrimazole. The $O.D._{600}$ values for the wells that did not have increased fluorescence indicated that the under these conditions, the clotrimazole inhibited growth of both the target and decoy cells. The fluorescent signals from the 1:1000 target: decoy ratio produced significant fluorescent signals at 0.2–5.6 µg/ml clotrimazole at each of the cell densities. These results from this pilot study with clotrimazole demonstrate that this method is flexible, robust and could have significant advantages over traditional cell-based drug screening methodologies.

6.4. Determining of the Specificity of the TDS Assay in Yeast

To determine the specificity of the TDS assay, a chemical library of 560 compounds was screened using the same strains described in FIG. 2. The MicroSource library is a collection of 560 generic drugs. Four azole compounds that are known inhibitors of Erg11p, miconazole, sulconazole, ketoconazole and clotrimazole, are represented in the library. The conditions chosen for the co-culture were 25 target cells and 25,000 decoy cells (1:1000 target: decoy ratio) in a volume of 225 µl. These conditions produced the largest signal to noise ratio across the widest range of drug in FIG. 2.

Overnight cultures of the target and decoy cells were grown in YM medium plus 2% casamino acids to maintain selection for both episomal plasmids. One large batch of fresh medium (YM-Cas) was prepared that contained both target and decoy cells. This culture was diluted to $1 \times 10^5$ cells/ml and dispensed into the 96-well plates. Drugs from the Microsource library were then added to the cultures at two concentrations: 5 µg/ml plus 1% DMSO; and 0.5 µg/ml plus 0.1% DMSO. The plates were incubated at 30° C. Fluorescence and $O.D._{600}$ measurements were taken twice daily for ten days.

The only four drugs that produced a fluorescent signal from the co-cultures that was significantly higher than the no-drug treatments were the four known azole Erg11p inhibitors (FIG. 3). The co-cultures that were exposed to clotrimazole at both concentrations resulted in a significant fluorescent signal. The 5 µg/ml concentration of miconazole and sulconazole resulted in too severe a growth inhibition to produce positive signals, whereas the lower concentration (0.5 µg/ml) of both drugs produced significant positive signals. In contrast, the higher concentration of ketoconazole produced a significant signal while the lower concentration neither inhibited growth nor produced a positive signal.

Five compounds in the library severely inhibited growth at both concentrations. These included: cetylpyridinium chloride, dyclonine-HCl, ephedrine-HCl, phenylmercuric borate and thimerosol. Two compounds in the collection, calcein and acriflaviium-HCl, could not be assessed since these compounds were significantly fluorescent.

This experiment demonstrates two important aspects of this drug screening method. First, no false positives were detected in the assay. Out of 560 compounds, each, of which possesses biological activity in some species, the only four positive signals were from drugs known to inhibit the Erg11p. The second feature of this assay is the ease with which the assay could be adapted for any target of interest. The only specific requirement is that the target gene, when expressed at a high level, confer resistance to the corresponding inhibitor.

One limitation of the assay is its sensitivity to the concentration of the candidate drugs. For example, three of the four azoles only produced positive signals in only one of the two concentrations tested. This limitation could be overcome in one of two ways. The compound library could be screened at multiple concentrations. The strategy of this approach is to find at least one concentration where there is a significant difference between the growth rates of the target and decoy cells. The second, and more preferred, approach is to normalize the compound library based upon the compounds' minimum inhibitory concentration (MIC) values in yeast prior to screening. In this case, compounds that did not inhibit any essential cellular functions would be eliminated from the screen. The resulting normalized library could then be screened at a minimal number of concentrations.

7. INCREASING THE SENSITIVITY OF THE TDS ASSAY BY USING A SENSITIZED DECOY CELL

The sensitivity of the TDS is determined by the difference between the growth rates of the target and decoy strains. One way to increase the sensitivity of the assay is to use a decoy cell that has increased sensitivity with respect to a pre-selected target. This can be accomplished by reducing the dosage of the target gene in the decoy cell from two copies to one. Gaiever et al. have demonstrated that several different heterozygotes have increased sensitivity to the corresponding drugs (Gaiever, G Nat. Genet. 21:278–283). For example, the erg11/ERG11 heterozygote was shown to have increased sensitivity to fluconazole. The erg11/ERG 11 heterozygote can thus be used in a decoy in the TDS assay as described in Section 6.3 to increase the sensitivity of the screen. Other types of drug sensitizing mutations (e.g., point mutations in the target gene) can also be introduced into the decoy cell to increase the sensitivity of the TDS screen.

In some instances, the target gene is not essential for viability or for the normal growth of the test cell or organism. For example, the RCE1 gene of yeast is necessary for the proteolytic maturation of Ras2p protein and may represent a novel cancer target (Boyartchuk et al., 1997, Science 275:1796–1800). Nevertheless, deletion of the RCE1 gene does not cause an apparent growth defect.

Some slight modifications can be made to the yeast genome that can create a situation where Rce1p function can significantly positively influence the fitness of the cell. The ras2-23 allele is a temperature sensitive mutation in one of the two yeast RAS genes (Mitsuzawa et al., 1989, Genetics 123:739–748). Cells that harbor this mutation together with a ras1 mutation, can grow at 30° C. but not at 37° C. At 34° C., the growth of yeast harboring the ras2-23 allele is dependent upon Rce1p (Boyartchuk et al., 1997, Science 275:1796–1800).

A TDS screen can be set up to identify inhibitors of Rce1p by constructing the following cells. The target cell would possess loss of function mutations in RAS1 and RAS2. In place of RAS2 the cell would possess the ras2-23 allele. In addition, the target cell would also possess recombinant constructs that express RCE1 and GFP at high levels. The decoy cell would be isogenic to the target cell except for the recombinant constructs expressing RCE1 and GFP.

Since an rce1 mutant cell does not possess any overt phenotypes, it is expected that an inhibitor of Rce 1 p will not inhibit the growth of a wild-type cell. The growth of the target and decoy cells described in this example will however, depend upon Rce1p function. In the presence of an inhibitor of Rce1p, the target cell will be more resistant to the drug than the decoy cell and will eventually become the dominant member in the population and can easily be detected by assessing the emitted fluorescence.

8. IDETIFICATION OF INHIBITORS FOR A TARGET IN MAMMALIAN CELLS

The TDS screen can be applied to mammalian cell lines. Amplification of the dihydrofolate reductase gene (DHFR) in Chinese hamster ovary cells has been shown to confer resistance to methotrexate (Assaraf et al, 1989, J. Biol. Chem. 264:18326–18334). To perform a TDS screen for DHFR inhibitors, a GFP transgene is introduced into a cell line that is overexpressing the DHFR gene to create a target cell. The target cells are mixed in a 1:1000 ratio with wild-type decoy cells (no GFP, normal DHFR levels) and the mixture is grown in the presence of different compounds. Cultures with detectable levels of green fluorescence will have been grown in the presence of putative DHFR inhibitors.

9. IDENTIFICATION OF INGIBITORS FOR A TARGET IN THE NEMATODE CAENORGABDITIS ELEGANS

A strain of C. elegans is constructed that overexpresses β-tubulin, the protein encoded by the ben-1 locus, and GFP on a minichromosome by microinjection of a construct harboring the coding regions for the two proteins under the control of a constitutive promoter, for example a glycolitic pathway promoter. Offspring of the microinjected worms that exhibit germ line transmission of the transgenes are selected to generate the target strain. The decoy strain is the parental, uninjected strain. A pool of test compounds is spread on a plate of medium to which one worm from each of the decoy and target strains is added. One plate is treated with benzimidazole as a positive control, as benzimidazole is known to induce paralysis in and thus lower the fitness of wild type worms but not those that have dominant ben-i mutations (Driscoll et al., 1989, J. Cell Biol. 109:2993–3003). The plates are left to incubate for a generation time of 48 hours. The plates are examined to determine which of the pools of compounds increase the proportion of fluorescing worms relative to non-fluorescing worms. Test pools containing successively smaller numbers of test compounds are tested in the same manner, until the true inhibitors of β-tubulin activity are identified.

10. PERFORMING TDS SCREENS IN MICROBIAL ORGANISMS

The short generation time and availability of genetic tools makes microbial organisms ideally suited for the TDS screen. For example, the TDS screen can be used for identifying whether a compound has antibiotic activity. In a non-limiting example, the TDS screen can be used to identify novel growth inhibitors of mycobacteria such as Mycobacterium tuberculosis, the causative agent of tuberculosis. The nicotinamide adenine dinucleotide (NAD) metabolism pathway has been shown to be essential for the growth of the organism and is the target of anti-mycobacterial agents. For example, the drug isoniazid inhibits the growth of mycobacteria (for a review, see e.g., Miesel et al., 1998, Novartis Found. Symp. 217:209–221). The target gene of isoniazid is inhA, a gene encoding the enzyme isonicotinic acid hydrazide, which catalyzes the NAD-specific reduction of 2-trans-enoyl-acyl carrier protein, a necessary step in fatty acid synthesis. Mycobacteria that overexpress the inhA gene are resistant to isoniazid. Such overexpression can be laboratory-generated (Banerjee et al., 1994, Science 263:227–230) or naturally-occurring in clinically resistant strains of M. tuberculosis (Rouse et al., 1995, Antimicrob. Agents Chemother. 39:2472–2477). Thus, NAD-related pathways are useful target pathways for TDS screens for the identification of molecules with antitubercu-losis activity. While the inhA gene product can be used as the target in such a screen, it is preferable to identify drugs that inhibit related genes or gene products to which clinical strains are not resistant. One such gene is the quinolinic acid phosphoribosyltransferase (QAPRTase), which is an enzyme required for the biosynthesis of NAD (Sharma et al., 1998, Structure 6:1587–1599).

A TDS screen is used to identify inhibitors of NAD as follows: a target cell is generated by transforming a selected strain of M. tuberculosis (or related mycobacterium) with a high copy, ampicillin-selectable expression plasmid which expresses QAPRTase (which can be PCR amplified from the *M. tuberculosis* genome (Genbank Accession No. Z95586) and GFP under the control of a constitutive promoter. The decoy cell is generated by transforming the parent strain with an empty counterpart of the plasmid. The target cell and decoy cell are then mixed at a ratio of 1:1000 and dispersed into a 96-well microtiter plates at a total of approximately 10,0001 cells in a volume of 225 μl of LB medium with an ampicillin concentration of 125 μg/ml. Drugs from the Microsource library are individually added to the wells. At least one well in each plate receives no drug and serves as a negative control for measurement of signal to noise ratios. The cultures are grown at 37° C. for 48 hours with fluorescence and optical density measurements taken every two hours. Compounds that specifically inhibit the QAPRTase pathway produce detectable increases in fluorescence in those cultures that receive the compounds but not in the control cultures.

11. TDS SCREEN IN YEAST WITH A TARGET GENE THAT NEGATIVELY CONTRIBUTS TO CELL FITNESS

The following describes a TDS screen in yeast with a target gene that negatively contributes to cell fitness.

Step 1. Clone the human gene of interest into an overexpression plasmid.

Step 2. Transform the plasmid into a yeast strain and determine if the overexpression results in a loss of fitness (reduced growth rate). Several examples of overexpression lethality have been documented in the literature. In some cases, a specific genetic background may be required to obtain the desired overexpression reduced fitness phenotype. To rapidly screen all possible genetic backgrounds, the overexpression plasmid can be transformed into a population of bar-coded yeast deletion strains. Deletion mutants that are specifically affected by the overexpression of the human gene will be depleted from the population during a competitive growth experiment. The deletion strain with the greatest sensitivity to the overexpression construct is used as the target strain in the co-culture screen.

Step 3. Transform the yeast cell containing the human overexpression plasmid with a second plasmid that is overexpressing GFP. The resulting strain will be the target in the co-culture screen.

Step 4. Generate a decoy strain by transforming the two empty plasmids into an isogenic yeast strain.

Step 5. Mix the target and the decoy strains in a 1000:1 ratio and distribute the cells into 96-well plates where each well contains 200 μl of media with different inhibitors.

Step 6. Allow the mixture to grow to saturation and measure the final fluorescence levels of each of the wells. There are three possible outcomes of this co-culture assay:

1. The inhibitor blocks the growth of both the target and the decoy strains. The final culture will have a very low fluorescence signal.
2. The inhibitor does not affect the growth rates of either the decoy or the target cells. In this case, the decoy strain will out-compete the slower growing target strain and the final saturated culture will have a low fluorescence signal.
3. The inhibitor specifically targets the overexpressed human protein. This rescues the overexpression lethal phenotype and allows the target to grow at normal rates. Because the target strain starts out at a 1000:1 ratio over the decoy strain, this ratio will be maintained in the final saturated culture. The end result will be a very high fluorescence signal.

For helpful references, see e.g., Espinet et al., Jan. 11, 1995, Yeast 1:25–32; Lin et al., Nov. 13, 1992, Genetics 3:665–673.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for screening for a molecule that inhibits the activity or expression of a target protein encoded by a target gene, comprising:

(a) co-culturing a first cell or group of first cells and a second cell or group of second cells in the presence of a test molecule under a competitive growth condition, wherein the first cell has higher expression or activity of a target gene or a protein encoded by the target gene relative to the second cell, wherein said target protein positively contributes to the fitness of the first cell and second cell under said competitive growth condition, wherein the first cell further comprises and expresses a reporter protein or peptide encoded by a reporter gene that is not expressed in said second cell, wherein the first cell and second cell are of the same species and cell type, wherein the ratio of the number of first cells to second cells initially in the co-culture is equal to or less than one; and (b) measuring the activity or amount of the reporter protein or peptide, wherein an increase in activity or amount of the reporter protein or peptide relative to that in the co-culture in the absence of the test molecule suggests that the test molecule inhibits the activity or expression of the target protein.

2. The method according to claim 1, wherein the first cell has native levels of expression and activity of the target protein, and the second cell has reduced levels of said expression or activity relative to native levels of expression or activity for said second cell.

3. The method according to claim 1, wherein the first cell has elevated levels of expression or activity of the target protein relative to native levels of expression or activity for said first cell, and the second cell has native levels of expression and activity for said second cell.

4. The method according to claim 1, wherein the first cell has elevated levels of expression or activity of the target protein relative to native levels of expression or activity for said first cell, and the second cell has reduced levels of target protein expression or activity relative to native expression or activity for said second cell.

5. The method according to claim 2 or 4, wherein the reduced level of expression or activity of the target protein in the second cell has been generated by deleting one copy of the target gene in a diploid cell or mutating the target gene.

6. The method according to claim 2 or 4, wherein the reduced level of expression or activity of the target protein in the second cell is generated by expressing a dominant negative form of the target protein.

7. The method according to claim 2 or 4, wherein the reduced level of expression or activity of the target protein in the second cell is generated by lowering the activity or abundance of a target gene encoded RNA.

8. The method according to claim 7, wherein the activity or abundance of the target gene encoded RNA in said second cell is lowered by means of a ribozyme, an anti-sense nucleic acid, a double-stranded RNA or an aptamer.

9. The method according to claim 3 or 4, wherein an elevated level of target protein expression in said first cell is generated by recombinantly expressing the target protein.

10. The method according to claim 9, wherein the target protein is recombinantly expressed from a plasmid.

11. The method according to claim 9, wherein the target protein is recombinantly expressed from a chromosome.

12. The method according to claim 1, wherein the first and second cells are selected from the group consisting of a bacterial cell, a yeast cell, an insect cell and a mammalian cell.

13. The method according to claim 1, wherein a group of first cells and a group of second cells are co-cultured, and the group of first cells and group of second cells are two individual multicellular organisms, respectively, of the same species.

14. The method according to claim 13, wherein the species is *C. elegans*.

15. The method according to claim 1, wherein the reporter gene encodes a bioluminescent, chemiluminescent or fluorescent protein, and measuring the activity or amount of the reporter protein comprises measuring bioluminescence, chemiluminescence or fluorescence of said reporter protein.

16. The method according to claim 15, wherein the fluorescent protein is green fluorescent protein (GFP) or a fluorescent mutant thereof.

17. The method according to claim 16, wherein the fluorescent protein is a mutant GFP having an altered fluorescence wavelength, increased fluorescence, or both.

18. The method according to claim 17, wherein the mutant GFP is blue GFP.

19. The method according to claim 15, wherein the fluorescent protein is red fluorescent protein.

20. The method according to claim 15, wherein the fluorescent protein is yellow fluorescent protein.

21. The method according to claim 1, wherein the reporter gene encodes an enzyme.

22. The method according to claim 21, wherein the enzyme is β-galactosidase.

23. The method according to claim 1, wherein the reporter gene encodes a receptor.

24. The method according to claim 1, wherein the reporter gene encodes a transporter.

25. The method according to claim 1, wherein the amount of the reporter protein or peptide encoded by the reporter gene is measured by measuring the amount of an epitope of said reporter protein or peptide.

26. The method according to claim 25, wherein the reporter protein or peptide is selected from the group consisting of CD4, myc, glutathione-S-transferase, and hexa-histidine.

27. The method according to claim 25, wherein the reporter gene and target gene together comprise a fusion gene, wherein said fusion gene encodes an in-frame fusion of the reporter and target proteins.

28. The method according to claim 1, wherein the first and second cells are co-cultured at a ratio of 1:1.

29. The method according to claim 1, wherein the first and second cells are co-cultured at a ratio of 1:10.

30. The method according to claim 28 or 29, wherein a group of first cells and a group of second cells are co-cultured, and the group of first cells and group of second cells are two individual multicellular organisms, respectively, of the same species.

31. The method according to claim 30, wherein the species is *C. elegans*.

32. The method according to claim 1, wherein the first and second cells are co-cultured at a ratio of 1:100.

33. The method according to claim 1, wherein the first and second cells are co-cultured at a ratio of 1: 1000.

34. The method according to claim 1, wherein the first and second cells are co-cultured at a ratio of 1:10000.

35. The method according to claim 32, 33, or 34, wherein the first and second cells are selected from the group consisting of a bacterial cell, a yeast cell, an insect cell, a mammalian cell, and a plant cell.

36. The method according to claim 1, wherein the first cell is transformed with a nucleic acid comprising the reporter gene and target gene.

37. The method according to claim 1, wherein the first and second cells are co-cultured at a ratio of 1000:1.

38. A method for screening for a molecule that inhibits the activity or expression of a target protein encoded by a target gene, comprising:
  (a) co-culturing a first cell or group of first cells and a second cell or group of second cells in the presence of a test molecule under a competitive growth condition, wherein the first cell has higher expression or activity of the target protein relative to the second cell, wherein said target protein negatively contributes to the fitness of the first cell under said competitive growth condition, wherein the first cell further comprises and expresses a reporter protein or peptide encoded by a reporter gene that is not expressed in said second cell, wherein the first cell and second cell are of the same species and cell type, wherein the ratio of the number of first cells to second cells in the co-culture initially is greater than one; and
  (b) measuring the activity or amount of the reporter protein or peptide, wherein the lack of a decrease in activity or amount of the reporter protein or peptide relative to that in the co-culture in the absence of the test molecule suggests that the test molecule inhibits the activity or expression of the target protein.

39. The method according to claim 38, wherein the reporter gene encodes a bioluminescent, chemiluminescent or fluorescent protein, and measuring the activity or amount of the reporter protein comprises measuring bioluminescence, chemiluminescence or fluorescence of said reporter protein.

40. The method according to claim 38, wherein the fluorescent protein is GFP or a fluorescent mutant thereof.

41. A method for screening for a molecule that inhibits the activity or expression of a target protein encoded by a target gene, comprising:
  (a) co-culturing, in the presence of a test molecule under a competitive growth condition:
    (i) a first cell or group of first cells, wherein each of the first cell or group of first cells;
      (A) has elevated expression or activity of a first target protein or peptide expressed by a first target gene relative to a third cell; and (B) expresses a first reporter protein or peptide encoded by a first reporter gene, wherein said first reporter gene is not expressed in said third cell;

(ii) a second cell or group of second cells, wherein each of the second cell or group of second cells:

(A) has elevated expression or activity of a second target protein or peptide expressed by a second target gene relative to the third cell; and (B) expresses a second reporter protein or peptide encoded by a second reporter gene, wherein said second reporter gene is not expressed in said third cell; and (iii) a third cell or group of third cells, wherein each of the first and second target genes affects the fitness of the first cell or group of first cells, the second cell or group of second cells and the third cell or group of third cells, and wherein said first cell or group of cells, said second cell or group of second cells, and said third cell or group of third cells are of the same species and cell type; and (b) measuring the activity or amount of the first and second reporter protein or peptide in said first cell or group of first cells and said second cell or group of second cells, wherein an increase in the activity or amount of the first or second reporter protein or peptide during said co-culturing suggests that the test molecule inhibits the first or second target protein, respectively.

42. The method according to claim 41, wherein an elevated level of the first or second target protein is generated by recombinantly expressing the target gene.

43. The method according to claim 42, wherein said first or second target gene is recombinantly expressed from a plasmid.

44. The method according to claim 42, wherein said first or second target gene is recombinantly expressed from a chromosome.

45. The method according to claim 44, wherein an elevated level of first or second target protein activity is generated by expressing a constitutively active form of said first or second target protein.

46. The method according to claim 41, wherein the first cell, second cell and third cell are selected from the group consisting of a bacterial cell, a yeast cell, an insect cell, a mammalian cell, and a plant cell.

47. The method according to claim 41, wherein a group of first cells is co-cultured with a group of second cells and a group of third cells, and each of the group of first cells, the group of second cells and the group of third cells is an individual multicellular organism of the same species.

48. The method according to claim 47, wherein the species is *C. elegans*.

49. The method according to claim 41, wherein the first or second reporter gene encodes a bioluminescent, chemiluminescent or fluorescent protein, and measuring the activity or amount of said reporter protein comprises measuring bioluminescence, chemiluminescence or fluorescence of said reporter protein.

50. The method according to claim 49, wherein the fluorescent protein is GFP or a fluorescent mutant thereof.

51. The method according to claim 50, wherein the fluorescent protein is a mutant GFP having an altered fluorescence wavelength, increased fluorescence, or both.

52. The method according to claim 51, wherein the mutant GFP is blue GFP.

53. The method according to claim 49, wherein the fluorescent protein is red fluorescent protein.

54. The method according to claim 49, wherein the fluorescent protein is yellow fluorescent protein.

55. The method according to claim 41, wherein the first or second reporter gene encodes an enzyme.

56. The method according to claim 55, wherein the enzyme is $\beta$-galactosidase.

57. The method according to claim 41, wherein the first or second reporter gene encodes a receptor.

58. The method according to claim 41, wherein the first or second reporter gene encodes a transporter.

59. The method according to claim 41, wherein the amount of the first or second reporter protein or peptide is measured by measuring the amount of an epitope of said reporter protein or peptide.

60. The method according to claim 59, wherein the protein or peptide is CD4, myc, glutathione-S-transferase or hexahistidine.

61. The method according to claim 59, wherein the first or second reporter gene and first or second target gene together comprise a fusion gene, wherein said fusion gene encodes an in-frame fusion of the first reporter protein or peptide and the first target protein or the second reporter protein or peptide and the second target protein.

62. The method according to claim 41, wherein the first and second reporter genes are the same.

63. The method according to claim 62, further comprising re-screening a co-culture in which an increase in activity or amount of the reporter protein or peptide is detected in step (b), to detect whether the first cell or group of first cells or the second cell or group of second cells has the increased activity or amount of reporter protein or peptide.

64. The method according to claim 63, wherein the re-screening comprises conducting a polymerase chain reaction on nucleic acid from said co-culture.

65. The method according to claim 63, wherein the re-screening comprises selective growing of cells from the co-culture on auxotrophic media.

66. The method according to claim 41, wherein the first cell or group of first cells and the second cell or group of second cells is transformed with a nucleic acid comprising the first or second reporter gene and the first or second target gene, respectively.

67. The method according to claim 63, wherein the re-screening comprises:

(c) co-culturing, in the presence of a test molecule that caused the increased activity or amount of the reporter protein or peptide, the third cell or group of third cells and the first cell or group of first cells or the second cell or group of second cells; and (d) measuring the activity or amount of reporter protein or peptide of said first cell or group of first cells or said second cell or group of second cells, wherein an increase in the activity or amount of the reporter protein or peptide of said first cell or group of first cells or said second cell or group of second cells during said co-culturing of step (c) suggests that the molecule inhibits the first target protein or the second target protein, respectively.

68. The method according to claim 41, wherein the first reporter gene and the second reporter gene are different.

69. The method according to claim 68, wherein the first and second reporter proteins are different bioluminescent, chemiluminescent or fluorescent proteins, and measuring the activity or amount of the second and third reporter proteins comprises measuring bioluminescence, chemiluminescence or fluorescence of said reporter proteins.

70. The method according to claim 41, wherein the ratio of each of the first cell and the second cell to the third cell is 1:100.

71. The method according to claim 41, wherein the ratio of each of the first cell and the second cell to the third cell is 1:1000.

72. The method according to claim 41, wherein the ratio of each of the first cell and the second cell to the third cell is 1:10,000.

73. The method according to claim 70, 72, or 76, wherein the first cell, the second cell and the third cell are selected from the group consisting of a bacterial cell, a yeast cell, an insect cell, a mammalian cell, and a plant cell.

74. The method according to claim 41, wherein:
(a) each of the first and second target genes positively contributes to the fitness of the first cell or group of first cells, the second cell or groups of second cells, and the third cell or groups of third cells;
(b) the ratio of the number of third cells to each of the first cells or groups of third cells and the second cell or group of second cells initially in the co-culture is less than one; and
(c) an increase in the activity or amount of at least one reporter protein relative to that in the co-culture in the absence of the test molecule suggests that the test molecule inhibits one or more of said target proteins.

75. The method according to claim 41, wherein:
(a) each of the first and second target genes negatively contributes to the fitness of the first cell or group of first cells, the second cell or group of first cells, and third cell or group of third cells,
(b) the ratio of the number of third cells to each of the first cells or second cells is initially greater than one, and
(c) the lack of a decrease in activity or amount of the first or second reporter protein or peptide relative to that in the co-culture in the absence of the test molecule suggests that the test molecule inhibits target proteins, respectively.

76. A method for screening for a molecule that inhibits the activity or expression of a target protein encoded by a first target gene but not the activity or expression of a second protein encoded by a second, functionally similar gene, wherein the functionally similar gene is capable of rescuing a complete or partial loss of function mutation in the target gene, comprising:
(a) co-culturing a first cell or group of first cells and a second cell or group of second cells in the presence of a test molecule under a competitive growth condition, wherein the first cell expresses elevated levels of the target protein relative to the second cell and the second cell expresses elevated levels of the second protein relative to the first cell, wherein the target protein and the second protein both positively contribute to the fitness of the first cell and second cell, wherein the first cell further comprises and expresses a reporter protein or peptide encoded by a reporter gene that is not expressed in said second cell, wherein the first cell and second cell are of the same species and cell type; and
(b) measuring the activity or amount of the reporter protein or peptide, wherein an increase in activity or amount of the reporter protein during said co-culturing suggests that the test molecule inhibits the activity or expression of the target protein but not the activity or expression of the second protein.

77. The method according to claim 76, wherein the functionally similar gene is a homolog of the target gene from another species.

78. The method according to claim 76, wherein the functionally similar gene encodes a protein from the same species.

79. The method according to claim 78, wherein said protein is an isozyme of the protein encoded by the target gene.

80. The method according to claim 78, wherein said protein is a splice variant of the protein encoded by the target gene.

81. The method according to claim 78, wherein said protein is a point mutant of the protein encoded by the target gene.

82. The method according to claim 76, wherein the elevated level of gene expression of said target gene or functionally similar gene is generated by-recombinantly expressing the gene.

83. The method according to claim 82, wherein the target gene or functionally similar gene is recombinantly expressed from a plasmid.

84. The method according to claim 82, wherein the target gene or functionally similar gene is recombinantly expressed from a chromosome.

85. The method according to claim 76, wherein the first and second cells are selected from the group consisting of a bacterial cell, a yeast cell, an insect cell, a mammalian cell, and a plant cell.

86. The method according to claim 76, wherein a group of first cells and group of second cells are co-cultured, and the group of first cells and the group of second cells are two individual multicellular organisms, respectively, of the same species.

87. The method according to claim 86, wherein the species is *C. elegans*.

88. The method according to claim 76, wherein the reporter gene encodes a bioluminescent, chemiluminescent or fluorescent protein, and measuring the activity or amount of the protein comprises measuring bioluminescence, chemiluminescence or fluorescence of said reporter protein.

89. The method according to claim 98, wherein the fluorescent protein is GFP or a fluorescent mutant thereof.

90. The method according to claim 88, wherein the fluorescent protein is a mutant GFP having an altered fluorescence wavelength, increased fluorescence, or both.

91. The method according to claim 90, wherein the mutant GFP is blue GFP.

92. The method according to claim 88, wherein the fluorescent protein is red fluorescent protein.

93. The method according to claim 88, wherein the fluorescent protein is yellow fluorescent protein.

94. The method according to claim 76, wherein the reporter gene encodes an enzyme.

95. The method according to claim 94, wherein the enzyme is β-galactosidase.

96. The method according to claim 76, wherein the reporter gene encodes a receptor.

97. The method according to claim 76, wherein the reporter gene encodes a transporter.

98. The method according to claim 76, wherein the amount of reporter protein or peptide is measured by measuring the amount of an epitope of said reporter protein or peptide.

99. The method according to claim 98, wherein the reporter protein or peptide is CD4, myc, glutathione-S-transferase or hexahistidine.

100. The method according to claim 76, wherein the reporter gene and target gene together comprise a fusion gene, wherein said fusion gene encodes an in-frame fusion of the reporter protein or peptide and the target protein.

101. The method according to claim 76, wherein the first and second cells are co-cultured at a ratio of 1:1.

102. The method according to claim 101, wherein a group of first cells and a group of second cells are co-cultured, and the group of first cells and group of second cells are two individual multicellular organisms, respectively, of the same species.

103. The method according to claim 102, wherein the species is *C. elegans*.

104. The method according to claim 76, wherein the first and second cells or groups of cells are co-cultured at a ratio of 1:100.

105. The method according to claim 76, wherein the first and second cells or groups of cells are co-cultured at a ratio of 1:1000.

106. The method according to claim 104 or 105, wherein the first and second cells are selected from the group consisting of a bacterial cell, a yeast cell, an insect cell, a mammalian cell, and a plant cell.

107. The method according to claim 76, wherein the first cell is transformed with a nucleic acid comprising the reporter gene and target gene.

* * * * *